(12) United States Patent
Petolino et al.

(10) Patent No.: US 9,249,422 B2
(45) Date of Patent: Feb. 2, 2016

(54) PROTEIN PRODUCTION IN PLANT CELLS AND ASSOCIATED METHODS AND COMPOSITIONS

(75) Inventors: Joseph F. Petolino, Zionsville, IN (US); Qihua C. Cai, Westfield, IN (US); Weiting W. Ni, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 641 days.

(21) Appl. No.: 12/509,766

(22) Filed: Sep. 9, 2009

(65) Prior Publication Data

US 2011/0008833 A1 Jan. 13, 2011

Related U.S. Application Data

(60) Provisional application No. 61/088,098, filed on Aug. 12, 2008.

(51) Int. Cl.
*C12N 15/09* (2006.01)
*C12N 15/82* (2006.01)

(52) U.S. Cl.
CPC .................................. *C12N 15/8201* (2013.01)

(58) Field of Classification Search
None
See application file for complete search history.

(56) References Cited

U.S. PATENT DOCUMENTS

2002/0069431 A1 6/2002 Broadway et al.
2006/0064783 A1* 3/2006 Usami et al. .................. 800/289
2007/0134796 A1 6/2007 Holmes

OTHER PUBLICATIONS

Ma et al., Nature Reviews, 4:794-805, 2003.*
PCT Search Report for International Application No. PCT/US2009/052218, mailed Feb. 4, 2010, 1 page.
PCT Written Opinion for International Application No. PCT/US2009/052218, mailed Feb. 4, 2010, 6 pages.

* cited by examiner

*Primary Examiner* — Nancy T Vogel
(74) *Attorney, Agent, or Firm* — Eric J. Kraus; TraskBritt, P.C.

(57) ABSTRACT

The present invention relates to methods and compositions for the expression of protein. Embodiments of methods may comprise the cleavage and repair of a nucleotide sequence encoding a highly expressed protein leading to a reduction in the expression of the highly expressed protein.

26 Claims, 8 Drawing Sheets

Figure 4B: Molecular analysis: PCR

```
                         SEQUENCE LISTING

<160> NUMBER OF SEQ ID NOS: 21

<210> SEQ ID NO 1
<211> LENGTH: 12
<212> TYPE: DNA
<213> ORGANISM: Artificial Sequence
<220> FEATURE:
<223> OTHER INFORMATION: CHN50 Target Sequence

<400> SEQUENCE: 1
tccgaccagg ag                                                        12

<210> SEQ ID NO 2
<211> LENGTH: 28
<212> TYPE: PRT
<213> ORGANISM: Artificial Sequence
<220> FEATURE:
<223> OTHER INFORMATION: ZFN Binding Motif

<400> SEQUENCE: 2

Arg Ser Ala Asn Leu Ala Arg Arg Ser Asp Asn Leu Arg Glu Asp Arg
1               5                   10                  15

Ser Asn Leu Ser Arg Asp Ser Ser Asp Arg Lys Lys
            20                  25

<210> SEQ ID NO 3
<211> LENGTH: 12
<212> TYPE: DNA
<213> ORGANISM: Artificial Sequence
<220> FEATURE:
<223> OTHER INFORMATION: CHN50 Target Sequence

<400> SEQUENCE: 3
tcggacgagg cc                                                        12
```

```
<210> SEQ ID NO 4
<211> LENGTH: 28
<212> TYPE: PRT
<213> ORGANISM: Artificial Sequence
<220> FEATURE:
<223> OTHER INFORMATION: ZFN Binding Motif

<400> SEQUENCE: 4

Asp Asn Arg Asp Leu Ile Arg Arg Ser Asp Leu Ser Arg Asp Arg
1               5                   10                  15

Ser Asn Leu Ser Arg Arg Asn Asp Asp Arg Lys Lys
            20                  25

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
caatgtggtt cgcaggcggg                                            20

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
gctcattaac acatctattg tggacaaagt c                               31

<210> SEQ ID NO 7
<211> LENGTH: 36
<212> TYPE: DNA
<213> ORGANISM: Artificial Sequence
<220> FEATURE:
<223> OTHER INFORMATION: Primer

<400> SEQUENCE: 7
ctcctggtcg gaaattaggc ctatttcgga cgaggc                          36

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
gcctcgtccg aaataggcct aatttccgac caggag                          36

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ccttgcactt cgccacttta ctac                                       24
```

```
<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
agatctgggt aactggccta actg                                      24

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
gaggcttaga gaattcacag ctctt                                     25

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
gaaggcctat aacagcaacc acag                                      24

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
taaggatcca accatggctt ctcc                                      24

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
tgaaatatca ctggtgtctg gtggt                                     25

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
tacccttggt tggttgctga ggtt                                      24

<210> SEQ ID NO 16
<211> LENGTH: 25
<212> TYPE: DNA
<213> ORGANISM: Artificial Sequence
<220> FEATURE:
<223> OTHER INFORMATION: Primer
```

```
<400> SEQUENCE: 16
tctggttcgg aattacacca tctac                                        25

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
ctttcttcgc ccaaacctc                                               19

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
ggaccatctg gtgctgttg                                               19

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
cccagatcat gtttgagacc t                                            21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ggaagcgcat atccctcata g                                            21

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
ctagtggtcg tactactggt attgtgct                                     28
```

PROTEIN PRODUCTION IN PLANT CELLS AND ASSOCIATED METHODS AND COMPOSITIONS

CROSS-REFERENCE TO RELATED APPLICATION

This application claims the benefit of U.S. Provisional Patent Application No. 61/088,098, filed on Aug. 12, 2008, which is expressly incorporated by reference herein.

FIELD OF THE INVENTION

The present invention relates to molecular biology, more particularly to genetic modification through the utilization of zinc finger nucleases.

BACKGROUND OF THE INVENTION

Targeted genome modification of plants has been a long-standing and elusive goal of both applied and basic research. In principle, the ability to direct transgene integration to specific sites within the plant genome and to make precise nucleotide sequence alterations would not only provide a powerful tool for basic studies of plant gene function but would also directly enhance the development of new crop varieties. However, current approaches to plant genome modification involve either the random integration of DNA into arbitrary genomic locations, as originally described in 1983, or the indiscriminant alteration of gene sequences with chemical or physical mutagens.

Although well established in yeast and moss, gene targeting—the introduction of foreign DNA into a predetermined genomic location—remains a significant challenge in higher plants. Site-specific transgene integration occurs at a very low frequency in plant cells as compared to random integration, even when the incoming DNA contains large stretches of sequence homologous to host DNA. For example, a highly efficient *Agrobacterium*-based transfection system and herbicide selection resulted in gene targeting frequencies of up to $5 \times 10^{-4}$ in rice. Attempts to enhance gene targeting efficiencies in plants have included the use of negative selection markers, and the use of plants genetically engineered to exhibit higher targeting frequencies. These efforts notwithstanding, random DNA integration via non-homologous processes continues to be a major impediment to gene targeting in plants. Given the general utility envisioned for targeted gene addition in the modification of crops for agricultural and industrial biotechnology, a solution to this problem is sorely needed.

In this regard, substantial increases in the frequency of gene targeting in a broad range of plant and animal model systems have been observed following the induction of a DNA double-strand break (DSB) at a specific genomic location in host cells, which stimulates a native cellular process, homology-directed DSB repair. Naturally occurring site-specific endonucleases whose recognition sites are rare in the plant genome have been used in this manner to drive transgene integration into a target sequence previously transferred into the plant genome via random integration. These studies highlighted the potential of targeted DSB induction to stimulate gene targeting in plant cells, though the challenge of introducing a DSB in a native locus remains.

In animal cells, the solution to targeted induction of a DSB at a native genomic location is provided by zinc finger nucleases (ZFNs). The C2H2 zinc finger was discovered in the amphibian transcription factor TFIIIA, and has since been found to be the most common DNA recognition motif in all species of metazoa. The X-ray crystal structure of the C2H2 ZFP, Zif268, revealed a strikingly syllabic mode of protein-DNA recognition, with each zinc finger specifying a 3 or 4 bp subsite in the context of a tandem arrangement, and suggested the possibility of using this peptide motif as a scaffold for DNA binding domains with novel specificities. Since then, a large number of ZFPs engineered to bind novel sequences have been successfully used in many different laboratories in the context of artificial transcription factors and other functional chimeric proteins.

Zinc finger nucleases are produced by fusing a zinc finger protein with a sequence-independent nuclease domain derived from the Type IIS restriction endonuclease FokI. Beginning with studies in Xenopus and fruit flies, a DSB targeted by ZFNs to an investigator-specified DNA sequence has been shown to stimulate homology-directed DNA repair in a range of model systems. More recently, engineered zinc finger nucleases have emerged as flexible and effective tools for native gene correction and disruption in human, hamster, nematode, and zebrafish. Moreover, and of relevance to the current work, ZFNs have been used to drive high-efficiency targeting (or "gene addition") to a native locus without any measurable increase in the rate of random integration, initially in transfected and subsequently in primary human cells.

Importantly, initial attempts at using ZFNs in plants have been equally successful. In *Arabidopsis*, ZFNs have been demonstrated to introduce targeted mutations at frequencies as high as 20%. Furthermore, in tobacco, using a pre-engineered target site, it was shown that zinc finger nucleases may target specific sites pre-integrated into a plant genome and facilitate site-specific DNA integration, in agreement with findings made with endonucleases such as I-SceI.

BRIEF SUMMARY OF THE INVENTION

The following embodiments and aspects thereof are described in conjunction with systems, tools and methods that are meant to be exemplary and illustrative, not limiting in scope.

Certain embodiments of the invention include methods of producing a protein of interest, one example method comprising: providing a cell comprising a first nucleic acid sequence encoding a highly expressed protein; providing to the cell at least one ZFN capable of inducing a double-strand break in the first nucleic acid sequence in the region encoding the highly expressed protein; cleaving the first nucleic acid with at least one ZFN to generate a double-strand break; providing to the cell a donor sequence; repairing the double-strand break through the insertion of the donor sequence at or across the cleavage site; wherein inserting the donor sequence into the first nucleic sequence decreases expression of the nucleic acid encoding highly expressed protein; providing to the cell a third nucleic acid sequence of interest; wherein the third nucleic acid sequence encodes a protein of interest; and expressing the third nucleic acid encoding the protein of interest.

A further example of a method comprises: providing a cell comprising a first nucleic acid sequence encoding a highly expressed protein; providing to the cell at least one ZFN capable of inducing a double-strand break in the first nucleic acid sequence in a region encoding the highly expressed protein; cleaving the first nucleic acid with at least one ZFN to generate a double-strand break; providing to the cell a donor sequence; repairing the double-strand break through the insertion of the donor sequence at or across the site of the cleavage site; wherein inserting the donor sequence into the first nucleic sequence decreases expression of the nucleic acid encoding the highly expressed protein; wherein the donor sequence encodes a protein of interest; and expressing the nucleic acid encoding the protein of interest.

An additional example of a method comprises: providing a cell comprising a first nucleic acid sequence encoding a highly expressed protein; providing to the cell at least one first ZFN capable of inducing a double-strand break in the first nucleic acid sequence encoding the highly expressed protein at a first location; providing to the cell at least one second ZFN capable of inducing a double-strand break in the first nucleic acid sequence in the sequence encoding the highly expressed protein at a second location; cleaving the first nucleic acid with the at least first ZFN to generate a first double-strand break; cleaving the first nucleic acid with the at least second ZFN to generate a second double-strand break; repairing the first and the second double-strand breaks so as to excise the portion of the first nucleic acid sequence between the first and second double-strand breaks; providing to the cell a donor sequence; wherein the donor sequence encodes a protein of interest; and expressing the nucleic acid encoding the protein of interest, wherein repairing the first and the second double-strand breaks decreases expression of the highly expressed protein.

In addition to the exemplary aspects and embodiments described above, further aspects and embodiments will become apparent by study of the following descriptions.

BRIEF DESCRIPTION OF THE DRAWINGS

FIG. 1 depicts designed ZFNs drive-targeted gene addition to the endochitinase locus.

DETAILED DESCRIPTION OF THE INVENTION

Figure 1A:
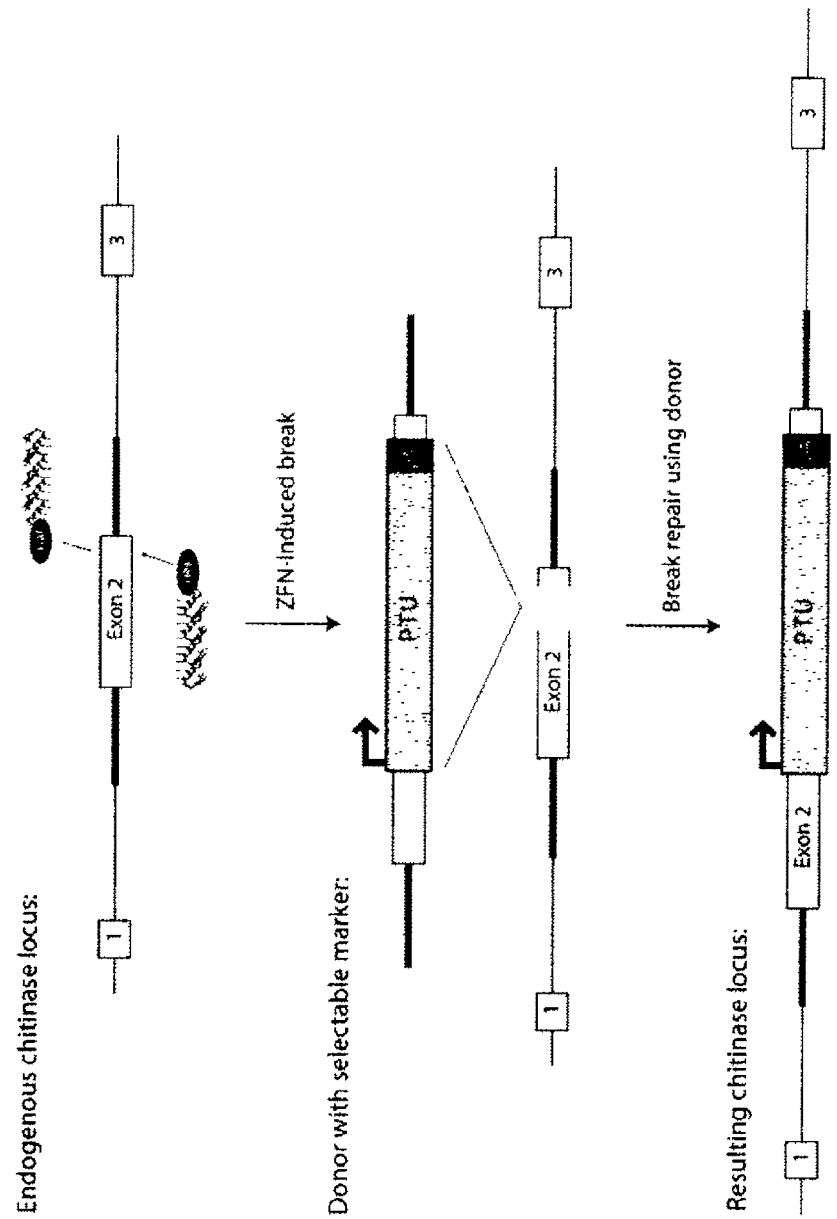
(FIG. 1A) Endochitinase targeting strategy.

Demonstrated herein is the use of ZFNs to cleave an unmodified endogenous plant locus. Further, the targeting of the unmodified endogenous gene for endochitinase in tobacco is demonstrated. To identify candidate ZFNs for this process, a yeast-based assay system that facilitates the rapid identification of active ZFN pairs was used. ZFNs identified by screening in this system are capable of cleaving the target site within the endogenous endochitinase gene in tobacco. Moreover, these ZFNs stimulated the targeted addition of a selectable marker gene into endogenous endochitinase locus.

In the description and tables that follow, a number of terms are used. To provide a clear and consistent understanding of the specification and claims, including the scope to be given such terms, the following definitions are provided:

Nucleic acid. The terms "nucleic acid," "polynucleotide," and "oligonucleotide" are used interchangeably and refer to a deoxyribonucleotide, ribonucleotide polymer, or other nucleotide or nucleoside polymer, in linear or circular conformation, and in either single- or double-stranded form. For the purposes of the present disclosure, these terms are not to be construed as limiting with respect to the length of a polymer. The terms may encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

Chromosome. A chromosome is a chromatin complex comprising all or a portion of the genome of a cell. The genome of a cell is often characterized by its karyotype, which is the collection of all the chromosomes that comprise the genome of the cell. The genome of a cell may comprise one or more chromosomes. An "episome" is a replicating nucleic acid, nucleoprotein complex or other structure comprising a nucleic acid that is not part of the chromosomal karyotype of a cell. Examples of episomes include plasmids and certain viral genomes. An "accessible region" is a site in cellular chromatin in which a target site present in the nucleic acid may be bound by an exogenous molecule that recognizes the target site. Without wishing to be bound by any particular theory, it is believed that an accessible region is one that is not packaged into a nucleosomal structure. The distinct structure of an accessible region may often be detected by its sensitivity to chemical and enzymatic probes, for example, nucleases. A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

Gene. A gene, for the purposes of the present disclosure, includes a DNA region encoding a gene product, as well as all DNA regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

Expression. Expression or gene expression are used interchangeably, and refer to the conversion of the information contained in a gene into a gene product. A gene product may be the direct transcriptional product of a gene (e.g., mRNA, tRNA, rRNA, antisense RNA, ribozyme, structural RNA or any other type of RNA) or a protein produced by translation of a mRNA. Gene products also include RNAs that are modified by processes such as capping, polyadenylation, methylation, and editing, and proteins modified by, for example, methylation, acetylation, phosphorylation, ubiquitination, ADP-ribosylation, myristilation, and glycosylation. "Modulation" of gene expression refers to a change in the activity of a gene. Modulation of expression may include, but is not limited to, gene activation and gene repression.

Protein. The terms "polypeptide," "peptide" and "protein" are used interchangeably to refer to a polymer of amino acid residues. The term also applies to amino acid polymers in which one or more amino acids are chemical analogues or modified derivatives of corresponding naturally occurring amino acids.

Sequence. The term "sequence" refers to a nucleotide sequence of any length, which may be DNA or RNA, may be linear, circular or branched and may be either single-stranded or double-stranded. The term "donor sequence" refers to a nucleotide sequence that is inserted into a genome. A donor sequence may be of any length, for example, between 2 and 25,000 nucleotides in length (or any integer value therebetween or thereabove), preferably between about 100 and 5,000 nucleotides in length (or any integer therebetween), more preferably between about 200 and 2,500 nucleotides in length.

Homologous sequence. Homologous sequence refers to a first sequence that shares a degree of sequence identity with a second sequence, and whose sequence may be identical to that of the second sequence. A "homologous, non-identical sequence" refers to a first sequence that shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination utilizing normal cellular mechanisms. Two homologous non-identical sequences may be any length and their degree of non-homology may be as small as a single nucleotide (e.g., for correction of a genomic point mutation by targeted homologous recombination) or as large as 10 or more kilobases (e.g., for insertion of a gene at a predetermined site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs may be used.

Recombination. Recombination refers to a process of exchange of genetic information between two polynucleotides. For the purposes of this disclosure, "homologous recombination (HR.)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer may involve mismatch correction of heteroduplex DNA that forms between the broken target and the donor, and/or "synthesis-dependent strand annealing" (SDSA), in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

Cleavage. "Cleavage," "inducing a double-strand break," and "cut" are used interchangeably and refer to the breakage of the covalent backbone of a DNA molecule. Cleavage may be initiated by a variety of methods including, but not limited to, enzymatic or chemical hydrolysis of a phosphodiester bond. Both single-stranded cleavage and double-stranded cleavage are possible, and double-stranded cleavage may occur as a result of two distinct single-stranded cleavage events. DNA cleavage may result in the production of either blunt ends or staggered ends. In certain embodiments, fusion polypeptides are used for targeted double-stranded DNA cleavage. A "cleavage domain" comprises one or more polypeptide sequences that possesses catalytic activity for DNA cleavage. A cleavage domain may be contained in a single polypeptide chain or cleavage activity may result from the association of two (or more) polypeptides. A "cleavage half-domain" is a polypeptide sequence that, in conjunction with a second polypeptide (either identical or different), forms a complex having cleavage activity (preferably double-strand cleavage activity). Double-strand break and double-stranded cleavage are used interchangeably.

Chromatin. Chromatin is the nucleoprotein structure comprising the cellular genome. Cellular chromatin comprises nucleic acid, primarily DNA, and protein, including histories and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone HZ is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

Binding. Binding refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}M^{-1}$ or lower. "Affinity" refers to the strength of binding: increased binding affinity being correlated with a lower $K_d$.

Operative linkage. The terms "operative linkage" and "operatively linked" (or "operably linked") are used interchangeably with reference to a juxtaposition of two or more components (such as sequence elements), in which the components are arranged such that both components function normally and allow the possibility that at least one of the components may mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked with a coding sequence, but need not be directly adjacent to it. For example, an enhancer is a transcriptional regulatory sequence that is operatively linked to a coding sequence, even though they are not contiguous. With respect to fusion polypeptides, the term "operatively linked" may refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

Zinc finger DNA binding protein. A zinc finger DNA binding protein, "ZFP" (or binding domain), is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains may be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261; and 6,785,613; see, also WO 98153058; WO 98153059; WO 98153060; WO 021016536 and WO 031016496; and U.S. Pat. Nos. 6,746,838; 6,866,997; and 7,030,215.

Genomic sequence. Genomic sequences include those present in chromosomes, episomes, organellar genomes (e.g., mitochondria, chloroplasts), artificial chromosomes and any other type of nucleic acid present in a cell such as, for example, amplified sequences, double minute chromosomes and the genomes of endogenous or infecting bacteria and viruses. Genomic sequences may be normal (i.e., wild-type) or mutant; mutant sequences may comprise, for example, insertions, deletions, translocations, 25 rearrangements, and/or point mutations. A genomic sequence may also comprise one of a number of different alleles.

Plant cells. Plant cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, rapeseed, and alfalfa. Plant cells may be from any part of the plant and/or from any stage of plant development.

Region of interest. A region of interest is any region of nucleic acid polymer, such as, for example, a gene or a non-coding sequence within or adjacent to a gene, in which it is desirable to bind an exogenous molecule. Binding may be for the purposes of targeted DNA cleavage and/or targeted recombination. A region of interest may be present in a chromosome, an episome, an organellar genome (e.g., mitochondrial, chloroplast), plasmid, an infecting viral genome, or any other nucleotide sequence, for example. A region of interest may be within the coding region of a gene, within transcribed non-coding regions such as, for example, leader sequences, trailer sequences or introns, or within non-transcribed regions, either upstream or downstream of the coding region. A region of interest may be as small as a single nucleotide pair or up to 25,000 nucleotide pairs in length, or any integral value of nucleotide pairs.

Disclosed herein are compositions and methods useful for targeted cleavage of plant cellular chromatin and for targeted alteration of a plant cellular nucleotide sequence, e.g., by targeted cleavage followed by intrachromosomal repair or by targeted cleavage followed by the insertion of a nucleotide sequence of interest (which may comprise one or more regions of homology with the cellular nucleotide sequence) into the cleavage site.

Embodiments include methods of producing a protein of interest. Embodiments of such methods may comprise providing a cell comprising a first nucleic acid sequence encoding a highly expressed protein, providing to the cell at least one ZFN capable of cleaving the first nucleic acid sequence, cleaving the first nucleic acid with at least one ZFN to generate at least one double-strand break, and repairing the at least one cleavage site in a manner so as to decrease expression of the highly expressed protein.

In further embodiments, the cell may be provided with a nucleotide sequence encoding a protein of interest. The protein of interest may be any proteinaceous molecule, including, but not limited to, nutrients, herbicide resistance, antibiotics, and/or therapeutic molecules as well as their precursors and enzymes or other proteins involved in their production.

Embodiments of the invention may comprise expression of the protein of interest. In some embodiments, a cell may be any kind of cell including, but not limited to, eukaryotic and prokaryotic cells. In other embodiments, the cell may be any cell containing a chloroplast. In further embodiments, the cell may be a plant cell. In other embodiments, the plant cell may be a dicotyledonous species. Particular dicotyledonous species may be selected from the group consisting of *Arabidopsis*, sunflower, cotton, rapeseed, tobacco, peanut and soybean. In yet further embodiments, the cell may be a tobacco cell. More particularly, the tobacco cell may be a cell of the genus *Nicotiana* and, more particularly, may be from the species *Nicotiana tabacum*. In alternative embodiments, the plant cell may be a monocotylendonous species. More particularly, the monocotyledonous species may be selected from the group consisting of maize, rice, sugarcane and wheat.

In some embodiments, the first nucleic acid sequence may encode a highly expressed protein, a more highly expressed protein, a very highly expressed protein, and/or a most highly expressed protein. Examples of "highly expressed proteins" include, but are not limited to, pathogen-related protein (PRP1), the wound-induced protein (WIP), osmotin, and endochitinase.

As used herein, "highly expressed protein" refers to a protein that is in the top 25% of proteins when the individual proteins expressed by a cell are ranked by the amount of protein or mRNA produced over a given period of time. As used herein, "more highly expressed protein" refers to a protein that is in the top 10% of proteins when the individual proteins expressed by a cell are ranked by the amount of protein or mRNA produced over a given period of time. As used herein, "very highly expressed protein" refers to a protein that is in the top 5% of proteins when the individual proteins expressed by a cell are ranked by the amount of protein or mRNA produced over a given period of time. As used herein, "most highly expressed protein" refers to a protein that is in the top 2% of proteins when the individual proteins expressed by a cell are ranked by the amount of protein or mRNA produced over a given period of time.

The number of copies of any protein produced over a given period of time may be determined or approximated by methods well known by those of ordinary skill in the art. By way of non-limiting example, cells may be pulsed with a radioactive amino acid (for example, but not limited to, methionine) for a given period of time before washing to remove any excess and immediate lysis of the cells. The contents may then be separated by normal means such as, but not limited to, gel electrophoresis or HPLC, and the relative radioactivity of the separated protein constituents determined and correlated to levels of protein production. By way of further non-limiting example, a radioactive nucleotide or other label may be given to cells for a discrete period of time and the mRNA from the cells isolated. The levels of individual mRNA may then be determined by northern blot or gene chip technology and correlated to provide a ranking of production.

In certain embodiments, ZFNs may comprise fusion proteins comprising a cleavage domain (or a cleavage half-domain) and a zinc finger binding domain, polynucleotides encoding these proteins and combinations of polypeptides and polypeptide-encoding polynucleotides. A zinc finger binding domain may comprise one or more zinc fingers (e.g., 2, 3, 4, 5, 6, 7, 8, 9 or more zinc fingers), and may be engineered to bind to any region of interest. Thus, by identifying a target region of interest at which cleavage or recombination is desired, one may, according to the methods disclosed herein, construct one or more fusion proteins comprising a cleavage domain (or cleavage half-domain) and a zinc finger domain engineered to recognize a target sequence in said region of interest. The presence of such a fusion protein (or proteins) in a cell will result in binding of the fusion protein(s) to its (their) binding site(s) and cleavage within or near said region of interest. Moreover, if an exogenous polynucleotide homologous to the region of interest is also present in such a cell, homology-directed repair occurs at a high rate between the double-strand break nucleotide sequence and the exogenous polynucleotide.

In particular embodiments, providing at least one ZFN to a cell may comprise directly providing one or more copies of a ZFN protein to the cell. Examples of techniques that may be used to directly provide a ZFN include, but are not limited to, microinjection, vesicle-mediated transfer using reagents such as, but not limited to, lipofectin and lipofectamine, and electroporation. In other embodiments, providing at least one ZFN to a cell may comprise providing the cell with a nucleic acid encoding the ZFN and allowing the cell to produce the ZFN from the nucleic acid encoding it.

In other embodiments, one or more ZFNs provided to the cell are capable of cleaving, individually, or in concert with other ZFNs, at or near one or more regions of interest. In some embodiments, one or more regions of interest may be within the coding sequence of a highly, more highly, very highly, or most highly expressed protein. In some embodiments, one or more regions of interest may be near and/or within a locus comprising a nucleotide sequence encoding a highly, more highly, very highly, or most highly expressed protein. In some embodiments, a nucleotide sequence may be double-strand break at a single region of interest. In further embodiments, a nucleotide sequence may be double-strand break at two or more regions of interest. In other embodiments, one or more of the double-strand breaks may be located in the coding sequence of a highly, more highly, very highly, or most highly expressed protein. In some embodiments, one or more of the double-strand breaks may be near and/or within a locus comprising a nucleotide sequence encoding a highly, more highly, very highly, or most highly expressed protein.

In a particular embodiment where at least two double-strand breaks are made, repairing the double-strand breaks may comprise removing the material between the double-strand breaks and rejoining the ends of the nucleotide sequence so as to excise the sequences between the double-strand breaks. In embodiments, the excised sequences may, without limitation, comprise sequences encoding all or a portion of a nucleotide sequence encoding a highly, more highly, very highly, or most highly expressed protein. In further embodiments, the excised sequences may, without limitation, comprise regulatory sequences effecting the expression of a highly, more highly, very highly, or most highly expressed protein. In such embodiments, the expression of the highly, more highly, very highly, or most highly expressed protein is decreased relative to levels of expression prior to cleaving.

In alternative embodiments where at least two double-strand breaks are made, repairing the double-strand breaks may comprise removing the material between the double-strand breaks replacing it with a donor sequence so as to substitute the sequences between the double-strand breaks with the donor sequence. In other embodiments, the removed sequences may, without limitation, comprise sequences encoding all or a portion of a nucleotide sequence encoding a highly, more highly, very highly, or most highly expressed protein. In further embodiments, the removed sequences may, without limitation, comprise regulatory sequences effecting the expression of a highly, more highly, very highly, or most highly expressed protein. In such embodiments, the expression of the highly, more highly, very highly, or most highly expressed protein is decreased relative to levels of expression prior to cleaving.

In embodiments where one double-strand break is made, repairing the double-strand break may comprise inserting a donor sequence into or across the double-strand break. In certain embodiments, the donor sequence may be inserted into the coding sequence of a highly, more highly, very highly, or most highly expressed protein. In embodiments, the insertion of such sequence may disrupt the transcription of the coding sequence of a highly, more highly, very highly, or most highly expressed protein through, by way of non-limiting example, the presence of an in-frame stop codon. In further embodiments, the donor may, without limitation, disrupt the function of regulatory sequences effecting the expression of a highly, more highly, very highly, or most highly expressed protein. In some embodiments, the expression of a highly, more highly, very highly, or most highly expressed protein is decreased relative to levels of expression prior to cleaving.

In yet other embodiments, the donor sequence may encode a protein of interest. In further embodiments, expression of the protein of interest from the donor sequence may be controlled, regulated by, or operatively linked to regulatory sequences present in the donor sequence and/or regulatory sequences present in the sequence into which the donor sequence was inserted. In additional embodiments, a nucleic acid sequence encoding a protein of interest may be provided to the cell separate to or in conjunction with the donor sequence. In some embodiments, the donor sequence may be contained within the same nucleic acid molecule as the sequence encoding a protein of interest.

In other embodiments, the nucleotide sequence encoding a highly, more highly, very highly, or most highly expressed protein nucleotide sequence encoding a highly, more highly, very highly, or most highly expressed protein may be located in, by way of non-limiting example, a genome, a plasmid, a cosmid, artificial chromosome, episome, or other nucleotide structure in the cell.

Practice of the methods, as well as preparation and use of the compositions disclosed herein, employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al., *MOLECULAR CLONING: A LABORATORY MANUAL*, Second edition, Cold Spring Harbor Laboratory Press, 1989, and Third edition, 2001; Ausubel et al., *CURRENT PROTOCOLS IN MOLECULAR BIOLOGY*, John Wiley & Sons, New York, 1987, and periodic updates; the series *METHODS IN ENZYMOLOGY*, Academic Press, San Diego; Wolffe, *CHROMATIN STRUCTURE AND FUNCTION*, Third edition, Academic Press, San Diego, 1998; *METHODS IN ENZYMOLOGY*, Vol. 304, "Chromatin" (P. M. Wassarman and A. P. Wolffe, eds.), Academic Press, San Diego, 1999; and *METHODS IN MOLECULAR BIOLOGY*, Vol. 119, "Chromatin Protocols" (P. B. Becker, ed.) Humana Press, Totowa, 1999.

Nucleic Acid Delivery to Plant Cells

As noted above, DNA constructs may be introduced into (e.g., the genome of) a desired plant host by a variety of conventional techniques. For reviews of such techniques see, for example, Weissbach & Weissbach, *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs may be introduced directly to plant tissue using biolistic methods, such as DNA particle bombardment (see, e.g., Klein et al. (1987), *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transfection techniques, including disarming and use of binary vectors, are well described in the scientific literature. See, for example, Horsch et al. (1984), *Science* 233:496-498, and Fraley et al. (1983), *Proc. Natl. Acad. Sci. USA* 80:4803.

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus. See, e.g., Chung et al. (2006), *Trends Plant Sci.* 11(1):1-4.

The virulence functions of the *Agrobacterium tumefaciens* host will direct the insertion of the construct and adjacent marker into the plant cell DNA when the cell is infected by the bacteria using binary T DNA vector (Bevan (1984), *Nuc. Acid Res.* 12:8711-8721) or the co-cultivation procedure (Horsch et al. (1985), *Science* 227:1229-1231). Generally, the *Agrobacterium* transfection system is used to engineer dicotyledonous plants (Mevan et al. (1982), *Ann. Rev. Genet.* 16:357-384; Rogers et al. (1986), *Methods Enzymol.* 118:627-641). The *Agrobacterium* transfection system may also be used to transform, as well as transfer, DNA to monocotyledonous plants and plant cells. See U.S. Pat. No. 5,591,616; Hemalsteen et al. (1984), *EMBO J.* 3:3039-3041; Hooykass-Van Slogteren et al. (1984), *Nature* 311:763-764; Grimsley et al. (1987), *Nature* 325:1677-179; Boulton et al. (1989), *Plant Mol. Biol.* 12:31-40; and Gould et al. (1991), *Plant Physiol.* 95:426-434.

Alternative gene transfer and transfection methods include, but are not limited to, protoplast transfection through calcium-, polyethylene glycol (PEG)- or electroporation-mediated uptake of naked DNA (see Paszkowski et al. (1984), *EMBO J.* 3:2717-2722; Potrykus et al. (1985), *Molec. Gen. Genet.* 199:169-177; From et al. (1985), *Proc. Natl. Acad. Sci. USA* 825824-5828; and Shimamoto (1989), *Nature* 338:274-276) and electroporation of plant tissues (D'Halluin et al. (1992), *Plant Cell* 4:1495-1505). Additional methods for plant cell transfection include microinjection, silicon carbide-mediated DNA uptake (Kaeppler et al. (1990), *Plant Cell Reporter* 9:415-418), and microprojectile bombardment (see Klein et al. (1988), *Proc. Natl. Acad. Sci. USA* 85:4305-4309; and Gordon-Kim et al. (1990), *Plant Cell* 2:603-618).

The disclosed methods and compositions may be used to insert exogenous sequences into a predetermined location in a plant cell genome. This is useful in as much as expression of an introduced transgene into a plant genome depends critically on its integration site. Accordingly, genes encoding, e.g., nutrients, antibiotics or therapeutic molecules may be inserted, by targeted recombination, into regions of a plant genome favorable to their expression.

Transfected plant cells that are produced by any of the above transfection techniques may be cultured to regenerate a whole plant that possesses the transfected genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and *Binding, Regeneration of Plants, Plant Protoplasts*, pp. 21-73, CRC Press, Boca Raton, 1985. Regeneration may also be obtained from plant callus, explants, organs, pollens, embryos or parts thereof. Such regeneration techniques are described generally in Klee et al. (1987), *Ann. Rev. of Plant Phys.* 38:467-486.

Nucleic acids introduced into a plant cell may be used to confer desired traits on essentially any plant. A wide variety of plants and plant cell systems may be engineered for the desired physiological and agronomic characteristics described herein using the nucleic acid constructs of the present disclosure and the various transfection methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine, fir, spruce); plants used in phytoremediation (e.g., heavy metal accumulating plants); oil crops (e.g., sunflower, rapeseed) and plants used for experimental purposes (e.g., *Arabidopsis*). Thus, the disclosed methods and compositions have use over a broad range of plants including, but not limited to, species from the genera Asparagus, Avena, Brassica, Citrus, Citrullus, Capsicum, Cucurbita, Daucus, Glycine, Gossypium, Hordeum, Lactuca, Lycopersicon, Malus, Manihot, Nicotiana, Oryza, Persea, Pisum, Pyrus, Prunus, Raphanus, Secale, Solanurn, Sorghum, Triticum, Vitis, Vigna, and Zea.

One of skill in the art will recognize that after the expression cassette is stably incorporated in transgenic plants and confirmed to be operable, it may be introduced into other plants by sexual crossing. Any of a number of standard breeding techniques may be used, depending upon the species to be crossed.

A transfected plant cell, callus, tissue or plant may be identified and isolated by selecting or screening the engineered plant material for traits encoded by the marker genes present on the transfecting DNA. For instance, selection may be performed by growing the engineered plant material on media containing an inhibitory amount of the antibiotic or herbicide to which the transfecting gene construct confers resistance. Further, transfected plants and plant cells may also be identified by screening for the activities of any visible marker genes (e.g., the P-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transfectants containing inserted gene constructs. These methods include but are not limited to: 1) Southern analysis or PCR amplification for detecting and determining the structure of the recombinant DNA insert; 2) Northern blot, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein may be observed by, for example, northern blots of the RNA (e.g., mRNA) isolated from the tissues of interest. Typically, if the amount of mRNA has increased, it may be assumed that the corresponding endogenous gene is being expressed at a greater rate than before. Other methods of measuring gene and/or CYP74B activity may be used. Different types of enzymatic assays may be used, depending on the substrate used and the method of detecting the increase or decrease of a reaction product or by-product. In addition, the levels of and/or CYP74B protein expressed may be measured immunochemically, i.e., ELISA, RIA, EIA and other antibody-based assays well known to those of skill in the art, such as by electrophoretic detection assays (either with staining or western blotting). The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein the progeny, clone, cell line or cell has the transgene or gene construct.

ZFNs and expression vectors encoding ZFNs may be administered directly to the plant for targeted cleavage and/or recombination.

Administration of effective amounts may be by any of the routes normally used for introducing ZFN into ultimate contact with the plant cell to be treated. The ZFNs are administered in any suitable manner, preferably with pharmaceutically acceptable carriers. Suitable methods of administering such modulators are available and well known to those of skill in the art and, although more than one route may be used to administer a particular composition, a particular route may often provide a more immediate and more effective reaction than another route.

Carriers may also be used and are determined in part by the particular composition being administered, as well as by the particular method used to administer the composition. Accordingly, there is a wide variety of suitable formulations of pharmaceutical compositions that are available (see, e.g., Remington's Pharmaceutical Sciences, 17th ed. 1985).

Applications

The disclosed methods and compositions for targeted cleavage may be used to induce mutations in a genomic sequence. Targeted cleavage may also be used to create gene knock-outs or gene knock-downs (e.g., functional genomics or target validation) and to facilitate targeted insertion of a sequence into a genome (i.e., sequence knock-in). Insertion may be by means of replacement of chromosomal sequences through, by way of non-limiting example, homologous recombination or by targeted integration, in which a new sequence (i.e., a sequence not present in the region of interest) is inserted at a predetermined target site. In certain examples, such new sequences may be flanked by sequences homologous to the region of interest in the chromosome. The same methods may also be used to replace a wild-type sequence with a mutant sequence or to convert one allele to a different allele.

Targeted cleavage of infecting or integrated plant pathogens may be used to treat pathogenic infections in a plant host, for example, by cleaving the genome of the pathogen such that its pathogenicity is reduced or eliminated. Additionally, targeted cleavage of genes encoding receptors for plant viruses may be used to block expression of such receptors, thereby preventing viral infection and/or viral spread in the plant.

Exemplary plant pathogens include, but are not limited to, plant viruses such as Alfarnoviruses, Alphacryptoviruses, Badnaviruses, Betaciyptoviruses, Bigeminiviruses, Bromoviruses, Bymoviruses, Capilloviruses, Carlaviruses, Carmoviruses, Caulimoviruses, Closteroviruses, Comoviruses, Cucurnoviruses, Cytorhabdoviruses, Dianthoviruses, Enamoviruses, Fabaviruses, Fijiviruses, Furoviruses, Hordeiviruses, Hybrigeminiviruses, Idaeoviruses, Ilaviruses, Ipomoviruses, Luteoviruses, Machlomoviruses, Macluraviruses, Marafiviruses, Monogeminiviruses, Nanaviruses, Necroviruses, Nepoviruses, Nucleorhabdoviruses, Oryzaviruses, Ourmiaviruses, Phytoreoviruses, Potexviruses, Potyviruses, Rymoviruses, satellite WAS, satelliviruses, Sequiviruses, Sobemoviruses, Tenuiviruses, Tobamoviruses, Tobraviruses, Tornbusviruses, Tospoviruses, Trichoviruses, Tymoviruses, Umbraviruses, Varicosaviruses and Waikaviruses; fungal pathogens such as smuts (e.g., Ustilaginales), rusts (Uredinales), ergots (Clavicepts pupurea) and mildew; molds (Oomycetes) such as *Phytophthora infestam* (potato blight); bacterial pathogens such as *Erwinia* (e.g., *E. herbicola*), *Pseudomonas* (e.g., *P. aeruginosa, P. syringae, P. fluorescense* and *P. putida*), *Ralstonia* (e.g., *R. solanacearum*), *Agrobacterium* and *Xanthomonas*; roundworms (Nematoda); and Phytomyxea (Polymyxa and Plasmodiophora).

The disclosed methods for targeted recombination production of a protein of interest may be used to replace any genomic sequence with a non-identical sequence. For example, a mutant genomic sequence may be replaced by its wild-type counterpart, thereby providing methods for treatment of plant diseases; provide resistance to plant pathogens; increase crop yields, etc. In like fashion, one allele of a gene may be replaced by a different allele using the methods of targeted recombination disclosed herein.

In many of these cases, a region of interest comprises a mutation, and the donor polynucleotide comprises the corresponding wild-type sequence. Similarly, a wild-type genomic sequence may be replaced by a mutant sequence, if such is desirable. For example, overexpression of an oncogene may be reversed either by mutating the gene or by replacing its control sequences with sequences that support a lower, non-pathologic level of expression. Indeed, any pathology dependent upon a particular genomic sequence, in any fashion, may be corrected or alleviated using the methods and compositions disclosed herein.

Targeted cleavage, insertion, excision, and/or recombination may also be used to alter noncoding sequences (e.g., regulatory sequences such as promoters, enhancers, initiators, terminators, splice sites) to alter the levels of expression of a gene product. Such methods may be used, for example, for therapeutic purposes, functional genomics and/or target validation studies.

Targeted modification of chromatin structure may be used to facilitate the binding of fusion proteins to cellular chromatin. In additional embodiments, one or more fusions between a zinc finger binding domain and a recombinase (or functional fragment thereof) may be used, in addition to or instead of the zinc finger-cleavage domain fusions disclosed herein, to facilitate targeted recombination. See, for example, co-owned U.S. Pat. No. 6,534,261 and Akopian et al. (2003), Proc. Natl. Acad. Sci. USA 100:8688-8691. In additional embodiments, the disclosed methods and compositions are used to provide fusions of ZFP binding domains with transcriptional activation or repression domains that require dimerization (either homodimerization or heterodimerization) for their activity. In these cases, a fusion polypeptide comprises a zinc finger binding domain and a functional domain monomer (e.g., a monomer from a dimeric transcriptional activation or repression domain). Binding of two such fusion polypeptides to properly situated target sites allows dimerization so as to reconstitute a functional transcription activation or repression domain.

Furthermore, as disclosed above, the methods and compositions set forth herein may be used for targeted integration of exogenous sequences into a region of interest in the genome of a cell, for example, in which cleavage enhances insertion via homology-dependent mechanisms (e.g., insertion of a donor sequence comprising an exogenous sequence together with one or more sequences that are either identical, or homologous but non-identical, with a predetermined genomic sequence (i.e., a target site).

The donor sequence may contain sufficient homology in the regions flanking the exogenous sequence to support homology-directed repair of a double-strand break in a genomic sequence, thereby inserting the exogenous sequence at the genomic target site. Therefore, the donor nucleic acid may be of any size sufficient to support integration of the exogenous sequence by homology-dependent repair mechanisms (e.g., homologous recombination). Without wishing to be bound by any particular theory, the regions of homology flanking the exogenous sequence are thought to provide the broken chromosome ends with a template for re-synthesis of the genetic information at the site of the double-stranded break. In certain embodiments, two of the identical sequences or two of the homologous but nonidentical sequences (or one of each) are present, flanking the exogenous sequence. An exogenous sequence (or exogenous nucleic acid or exogenous polynucleotide) is one that contains a nucleotide sequence that is not normally present in the region of interest.

Exemplary exogenous sequences include, but are not limited to, cDNAs, promoter sequences, enhancer sequences, epitope tags, marker genes, cleavage enzyme recognition sites and various types of expression constructs. See, for example, U.S. Pat. No. 6,833,252. Additional exemplary homing endonucleases include I-CeuI, PI-PspI, PI-Sce, I-SceIV, I-CsmI, I-PanI, I-SceII, I-PpoI, I-SceIII, ICreI, I-TevI, I-TevII and I-TaiIII. Their recognition sequences are known. See also U.S. Pat. No. 5,420,032; Belfort et al. (1997), *Nucleic Acids Res.* 25:3379-3388; Dujon et al. (1989), *Gene* 82:115-118; Perler et al. (1994), *Nucleic Acids Res.* 22:1125-1127; Jasin (1996), *Trends Genet.* 12:224-228; Gimble et al. (1996), *J. Mol. Biol.* 263:163-180; Argast et al. (1998), *J. Mol. Biol.* 280:345-353; and the New England Biolabs catalogue.

Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins that mediate enhanced cell growth and/or gene amplification (e.g., dihydrofolate reductase). Exemplary marker genes thus include, but are not limited to, β-glucuronidase (GUS), phosphinothricin N-acetyl transferase (PAT, BAR), neomycin phosphotransferase, β-lactamase, catechol dioxygenase, a-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase. In certain embodiments, targeted integration is used to insert a RNA expression construct, e.g., sequences responsible for regulated expression of micro RNA or siRNA. Promoters, enhancers and additional transcription regulatory sequences, as described above, may also be incorporated in a RNA expression construct.

The invention is further described with the aid of the following illustrative examples.

EXAMPLE 1

Generation of an Endochitinase Knock-Down Culture

The general strategy for generating an endochitinase knock-down culture is shown in FIG. 1A.

Zinc Finger Nuclease for Endochitinase Gene Cleavage

Zinc finger proteins designed against the coding sequence of the endochitinase gene λCHN50 (Fukuda et al., 1991, *Plant Molecular Biology* 16:1-10) are assembled as previously described (Miller, et al., 2007, *Nature Biotechnology* 25:778-785) to yield the following ZFP moieties: (listed as "target gene—ZFP name, target sequence, recognition α-helices"): λCHN50—ZFP-L, TCCGACCAGG AG (SEQ ID NO:1), RSANLARRSD NLREDRSNLS RDSSDRKK (SEQ ID NO:2); λCHN50—ZFP-R, TCGGACGAGG CC (SEQ ID NO:3), DNRDLIRRSD DLSRDRSNLS RRNDDRKK (SEQ ID NO:4). The zinc finger-FokI fusion protein genes are driven by a CsVMV promoter and 5'UTR (Verdaguer et al., 1996, *Plant Molecular Biology* 31:1129-1139). Also included in the cassettes are *N. tabacum* osmotin 5' and 3'UTRs (Merlo et al., 2005, US Patent 2005/0102713).

Construct for Targeted Integration into the Endochitinase Locus

Figure 2:
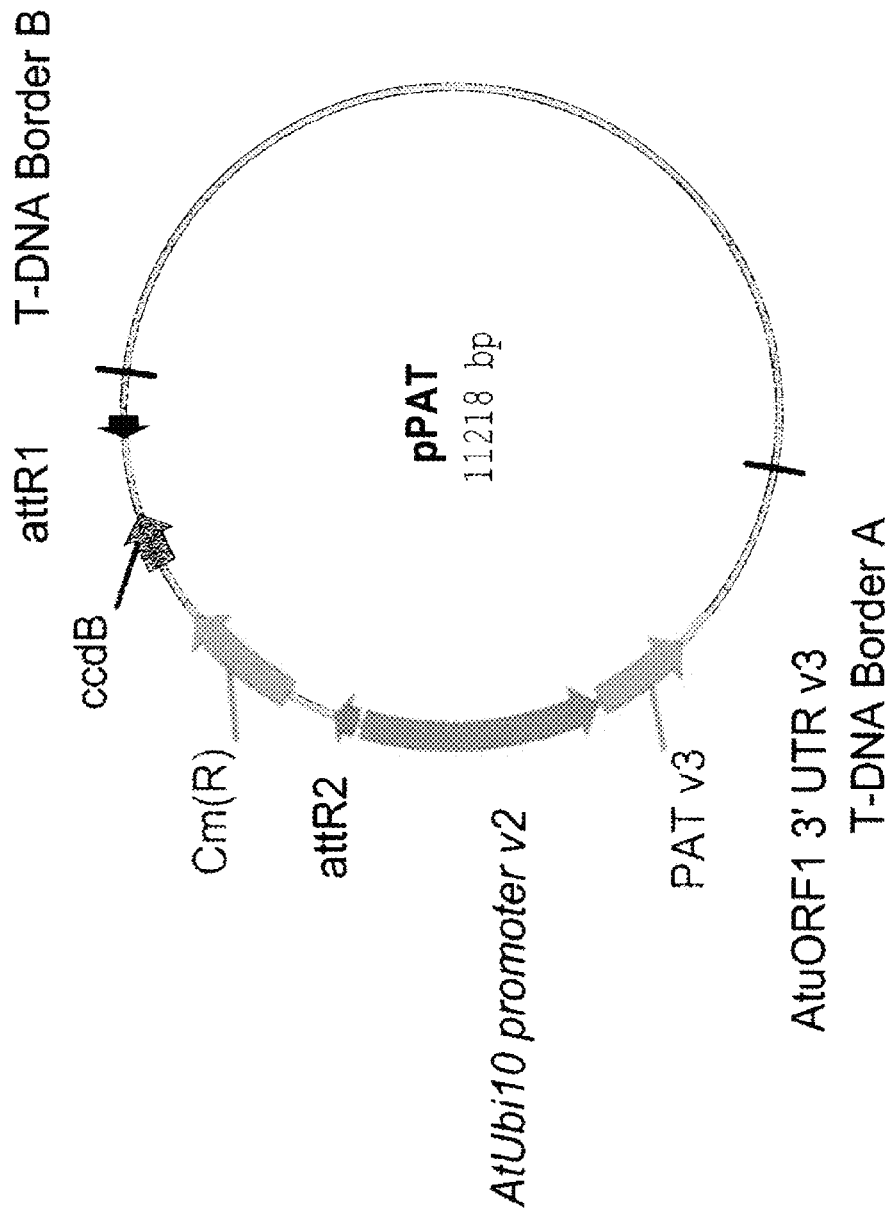
FIG. 2 is a schematic representation of plasmid pPAT.
Figure 3:
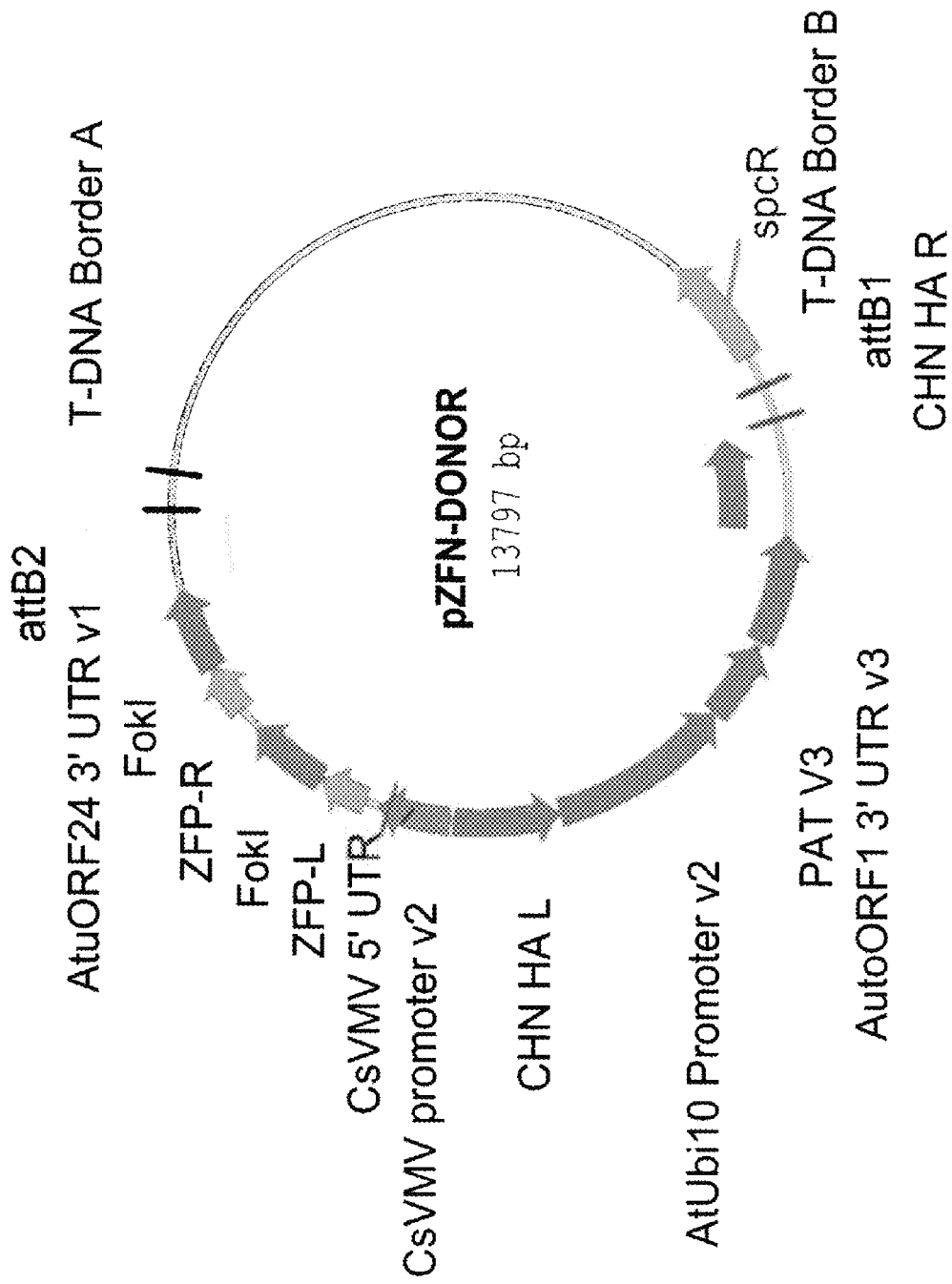
FIG. 3 is a schematic representation of plasmid pZFN-DONOR.

A 1,504 bp fragment of the endochitinase locus is generated by PCR from tobacco BY2 suspension culture genomic DNA and cloned into pCR4-topo (Invitrogen, Carlsbad, Calif.) using the following primers: 5'-CAATGTGGTT CGCAGGCGGG-3' (SEQ ID NO:5) and 5'-GCTCATTAAC ACATCTATTG TGGACAAAGT C-3' (SEQ ID NO:6). A novel StuI site is introduced between bases 750 and 751 of this fragment using the QuikChange Site-Directed Mutagenesis Kit (Stratagene) with the following primers: 5'-CTC-CTGGTCG GAAATTAGGC CTATTTCGGA CGAGGC-3' (SEQ ID NO:7) and 5'-GCCTCGTCCG AAATAGGCCT AATTTCCGAC CAGGAG-3' (SEQ ID NO:8). A promoter-PAT-UTR construct is then cut out of pPAT (FIG. 2) with PmeI and ligated into the donor linearized using StuI. To generate vectors containing both the ZFN genes and the donor sequence, first the donor DNA is cut with NotI and filled in using the Klenow fragment of DNA polymerase I. The linear DNA is then cut with PmeI and ligated into the zinc finger-FokI fusion protein genes expression cassette, which is prepared by digestion with SacII and is filled in using the Klenow fragment of DNA polymerase I. The ZFNs genes and the donor sequence are then moved into a base binary vector through Gateway LR recombination. The final expression vector, pZFN-DONOR, is shown in FIG. 3.

Generation of Endochitinase Knocked-Down Transgenic Events

A BY2 cell suspension culture is maintained in LSBY2 media containing LS basal salts (PhytoTechnology Labs L689), 170 mg/L $KH_2PO_4$, 30 g/L sucrose, 0.2 mg/L 2,4-D and 0.6 mg/L thiamine-HCL at a pH of 6.0. The cells are sub-cultured every seven days by adding 250 μL PCV to 50 mL of LSBY2 medium. The cultures are maintained in 250-mL flasks on a rotary shaker in the dark at 25±1° C. at 125 rpm.

In order to generate endochitinase knocked-down cell cultures, a flask of a four-day post-sub-culture BY2 suspension culture is divided into 10-12 four mL aliquots and co-cultivated in 100×25 mm Petri dishes with 100 µL *Agrobacterium* strain LBA4404 harboring pZFN-DONOR (FIG. 3) grown over night to an $OD_{600}$~1.5. Dishes are wrapped with NESCOFILM® (Azwell Inc., Osaka, Japan) and incubated at 25° C. without shaking for three days after which 12 mL of LSBY2 medium containing 500 mg/L carbenicillin is added. Following re-suspension of the tobacco cells, 1 mL aliquots are dispensed onto 100×25 mm plates of LS-basal medium containing 500 mg/L carbenicillin and 15 mg/L BIALA-PHOS® solidified with 8 g/L TC agar, and incubated unwrapped at 28° C. in the dark. This results in 120-144 selection plates. Individual BIALAPHOS®-resistant isolates appear 10-14 days after plating and are transferred to individual 60×20 mm plates (one isolate per plate) where they are assigned a number and maintained under selection as callus on a 14-day sub-culture schedule until needed for analysis and subsequent suspension culture initiation.

The BIALAPHOS®-resistant, transgenic events are sub-cultured onto fresh LS-basal medium containing 500 mg/L carbenicillin and 15 mg/L BIALAPHOS® solidified with 8 g/L TC agar every two weeks for a total of three passages. Suspension cultures are initiated by transferring 500 mg of seven-day-old proliferating transgenic callus into a 125-mL flask containing 25 ml LS-basal medium containing 15 mg/L BIALAPHOS®. The cells and liquid are mixed by pipetting three to five times with a 50 mL pipette to break up tissue, then agitated on a shaker at 125 rpm in the dark at 25±1° C. The suspension cultures are subcultured on a weekly basis by transferring 125 µL of packed cells into 25 mL of fresh medium. The suspension cultures are maintained in 125-mL flasks on a rotary shaker in the dark at 25±1° C. at 125 rpm.

Event Selection Based on Targeted Integration at the Endochitinase Locus

Genomic DNA is extracted from tobacco callus and cell suspension cultures using DNeasy 96 Plant kit (Qiagen, Valencia, Calif. USA) and quantified using PicoGreen ds DNA Quantitation kit (Molecular Probes, Eugene, Oreg. USA). An aliquot of 2 µL extracted genomic DNA is checked through agarose gel electrophoresis to ensure the DNA quality.

Figure 1B:
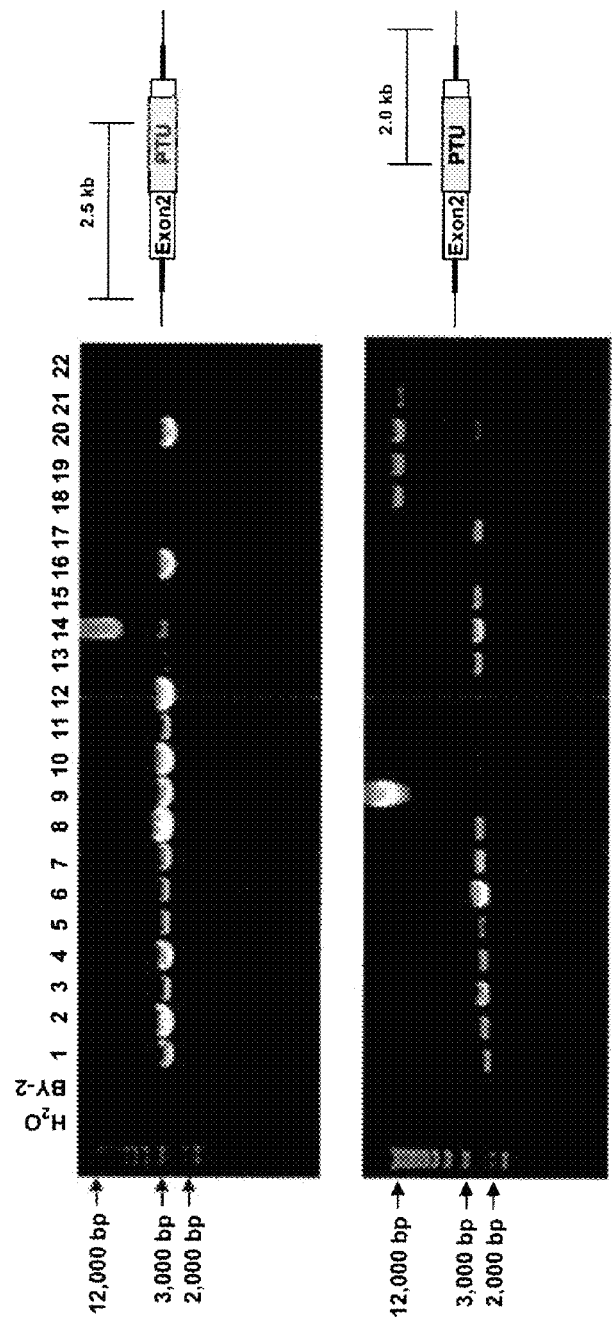
(FIG. 1B) PCR analysis: 5' (upper) and 3' (lower).

To confirm targeted integration at the endochitinase locus, an "in and out" nested PCR strategy is used to verify both 5' and 3' ends of the endochitinase locus. For the 5' end, nested PCR is performed using the following primers pair: forward primer—5'-CCTTGCACTT CGCCACTTTA CTAC-3' (SEQ ID NO:9) and reverse primer—5'-AGATCTGGGT AACTG-GCCTA ACTG-3' (SEQ ID NO:10) in the initial PCR, and forward primer—5'-GAGGCTTAGA GAATTCACAG CTCTT-3' (SEQ ID NO:11) and reverse primer—5'-GAAG-GCCTAT AACAGCAACC ACAG-3' (SEQ ID NO:12) in the nested PCR. Both forward primers anchor upstream and beyond the left homology arm (CHN HA L, FIG. 3), and both reverse primers are located within the coding sequence of the PAT gene. For the 3' end, the nested PCR is performed using the following primer pairs: forward primer—5'-TAAG-GATCCA ACCATGGCTT CTCC-3' (SEQ ID NO:13) and reverse primer—5'-TGAAATATCA CTGGTGTCTG GTGGT-3' (SEQ ID NO:14) in the initial PCR, and forward primer—5'-TACCCTTGGT TGGTTGCTGA GGTT-3' (SEQ ID NO:15) and reverse primer—5'-TCTGGTTCGG AATTACACCA TCTAC-3' (SEQ ID NO:16) in the nested PCR. Both forward primers anchor within the coding sequence of PAT gene, and both reverse primers are located downstream and beyond the right homology arm (CHN HA R, FIG. 3). Takara LA Taq polymerase (Takara, Japan) is used for these PCR reactions and the results are shown in FIG. 1B.

To further prove the targeted integration at the endochitinase locus, Southern blot analysis is carried out on the PCR prescreened events. For each sample, 10 µg of genomic DNA is digested with ApaLI and MscI restriction enzymes, separated on a 0.8% agarose gel, transferred and cross-linked onto a nylon membrane. A specific probe amplified from endochitinase Exon 1 and the sequence beyond the left side homology arm (CHA HA L) is labeled with $P^{32}$ dCTP using the Prime-It RmT Random Primer Labeling Kit (Stratagene, La Jolla, Calif., USA) and hybridized to the membrane overnight at 65° C. The hybridized membrane is then washed in graduated, increased stringency with the final wash in 0.1×SSC with 01% SDS at 65° C. for 30 minutes. The membranes are analyzed by a BAS 1500 imaging plate scanner (Fuji Photo Film, Tokyo, Japan) or exposed on an X-ray film for a few days at −80° C.

Event Selection Based on Low/No Endochitinase Transcript

About 100 µg fresh cell sample is collected from each suspension culture and transferred into a 2-mL tube. After all samples are collected, the tubes are transferred to a microplate base and placed in ethanol/dry ice slurry for five minutes, and then stored at −80° C. prior to RNA isolation. To isolate the DNase-free total RNA, frozen samples are removed from the −80° C. freezer and placed on dry ice. One 3.2 mm stainless steel bead (BioSpec Products, Inc., Bartlesville, Okla.) is added per tube. 450 µL RNA lysis buffer, RLT, from RNEasy 96 kit (Qiagen, Inc., Valencia, Calif.) is also added to each tube. Cells are disrupted by shaking in a Kleco tissue pulverizer (Garcia Manufacturing, Visalia, Calif.) for three bursts of two minutes each at maximal speed. The disrupted cell lysis is then transferred into a 96-well plate. All subsequent RNA isolation is then performed using the Qiagen 96 RNEasy 96 kit following the manufacturer suggested protocol, except that an on-column DNase I digestion is performed using the RNase-free DNAse set (50) (Qiagen, Inc., Valencia, Calif.). After final column elution, RNA concentration is estimated by fluorometry using the Quant-IT Ribo Green RNA assay kit (Invitrogen Corp., Carlsbad, Calif.). Prior to assay, RNA concentration is adjusted to 200 ng/µL. Subsets of isolated RNA samples are chosen at random for visual assessment of RNA quality by agarose gel electrophoresis. The purified RNA is stored at −80° C.

The normalized total RNA is then analyzed by HT RNA chip (Caliper LS #60410/60411) according to manufacturer-suggested protocol. A total of 2 µL of RNA is denatured and mixed with 46 µL of sample buffer. First strand cDNA is prepared for 2 µL of normalized RNA (approximately 400 ng) using QUANTITECT® Reverse Transcription kit (Qiagen, #205313). The suggested protocol is followed, including DNase treatment with gDNA wipeout buffer, except that volumes are cut in half for all components (10 µL reaction). Following cDNA synthesis, samples are diluted 1:3 with the addition of 20 µL of nuclease-free water. Samples are stored frozen at −20° C. until assayed.

Endochitinase (λCHN50) mRNA is assayed using Roche UPL format. The assay is designed such that the 61 nt amplicon spans a 272 bp intron. Assay primer sequences are CHN88S=5'-CTTTCTTCGC CCAAACCTC-3' (SEQ ID NO:17) and CHN88A=5'-GGACCATCTG GTGCTGTTG-3' (SEQ ID NO:18). The 6-FAM-labeled probe used is universal probe library (UPL) #88 (Roche Applied Science, #04689135001). Actin (BY2ACT89) mRNA is assayed using hydrolysis probe format (TAQMAN®). The assay is designed such that the 157 nt amplicon spans a putative splice junction 69 bp downstream of the forward primer binding site. Assay primers and probe sequence information are as follows: BY2ACT89S=5'-CCCAGATCAT GTTTGAGACC T-3' (SEQ ID NO:19), BY2ACT89A=5'-GGAAGCGCAT ATC-CCTCATA G-3' (SEQ ID NO:20), BY2ACTFQ (probe)=/5'Cy5/CTAGTGGTCGTACTACTG*GTATTGTGCT/3' (SEQ ID NO:21) BHQ2/. The probe sequence spans the putative splice junctions at the asterisk.

Reactions are carried out using the LIGHTCYCLER® 480 Probes Master—5×1 mL (2×) kit (Roche Applied Science, #04707494001). Reactions consist of 8 µL of mix (5 µL 2× buffer, 0.25 µL of 10 µM CHN88S primer, 0.25 µL CHN88A primer, 0.1 µL UPL#88 probe, 0.25 µL of 10 µM BY2ACT89S primer, 0.25 µL of 10 µM BY2ACT89A primer, 0.25 µL of 5 µM BY2ACT89FQ probe and 1.65 µL of nuclease-free PCR grade water) and 2 µL of diluted cDNA sample. Cycling is done following initial 95° C. incubation for ten minutes, and consisted of 40 cycles of denaturation at 95° C. for ten seconds, annealing at 60° C. for 25 seconds and acquisition at 72° C. for one second.

Post-reaction analysis is performed using relative quantification software (LIGHTCYCLER® 480 software release 1.5.0). For this, a two-fold serial dilution is prepared of wild-type BY2 tobacco seven-day suspension cDNA and included in the run to determine the amplification efficiencies for the endochitinase and actin targets in the multiplexed reactions. Estimated reaction efficiencies are then used to determine the crude ratio of endochitinase target to actin reference for each unknown sample. Data is then normalized to one BY2 sample from each time point, randomly selected as calibrator event, to determine relative expression compared to wild-type BY2.

Assay validation is performed using one column of seven-day suspension samples. Corresponding stock RNA is diluted (2 µL into 30 µL) in water to mimic the cDNA synthesis step. Subsequently, 2 µL of either diluted RNA or cDNA is assayed by relative quantification. Sample H4 cDNA (BY-2) is used as calibrator. No Ct is able to be calculated within 40 cycles for the RNA samples, while all corresponding cDNA samples give Cts for both λCHN50 target and BY2ACT89 reference in the range of 22-25 cycles. DNA is examined by Caliper LS Lab Chip DNA analysis to verify specificity of reaction products based on size. To determine variability in base culture expression, a series of eight non-transfected BY2 seven-day suspension samples are harvested from a single flask and RNA is isolated in single-tube format for each. RNA is adjusted to 200 ng/µL and cDNA is prepared as described above. Samples are then assayed by relative quantity using one sample randomly chosen as calibrator. The normalized λCHN50 expression in the remaining seven samples differs from the calibrator by only 2-14%.

Event Selection Based on Low/No Endochitinase Protein

For protein extraction, suspension cells are homogenized in phosphate buffer (pH 6.8) at 4° C. using a Microfluidics M110EH cell disrupter. The Bradford method is used for protein quantification with BSA used as a standard. Isoelectric focusing (IEF) is performed using Bio-Rad IPG stript and Protein IEF Cell, module 90-240 VAC. Additional CHAPS are added into the alkalized sample to a final concentration of 2%; and carrier ampholytes, pH 3-10, are added to a final concentration of 1%. IPG strips (pH 3-10, NL) are prepared by adding a 50 µL sample plus 160 µL of re-hydration solution. The re-hydration strips are placed in a focusing tray and covered with mineral oil. The re-hydration process lasts for ~24 hours. IEF is conducted under the following conditions: 300 V for one hour, 1,000 V for one hour, 2,000 V for two hours, 4,000 V for three hours and 8,000 V for eight hours for a total of—62,000 V-hours. After focusing, the strips are equilibrated first with equilibration buffer (6 M urea, 0.375 M Tris-HCl, pH 8.8, 2% SDS and 20% glycerol) plus 1% (w/v) DTT for ten minutes followed by equilibration buffer plus 2.5% (w/v) iodoacetamide for another ten minutes. After equilibration, the strips are loaded into 8-16% linear gradient Criterion Tris-HCl gels with 40% ethanol and 10% acetic acid for two hours, and stained with colloidal Coomassie blue solution for two days, then de-stained with 2% acetic acid for one day.

After SDS-PAGE, the bands of interest are excised from the gel and de-stained with 25% acetonitrile and 25 nM ammonium bicarbonate. The gel pieces are dehydrated with acetonitrile and dried with a speed-vacuum centrifuge. The dried gel pieces are re-hydrated and digested with sequencing grade trypsin (Promega, Catalog #V5280) at 37° C. overnight. After a brief centrifugation, the supernatant containing tryptic peptides is transferred to a clean siliconized tube. The peptides are cleaned with a C18 Zip Tip (Millipore, Catalog #2TC18S096). Mass spectral analysis is performed on a Voyager-DE STR MALDI-TOF mass spectrometer (PerSeptive Biosystems). One micro-liter of peptides (from Zip Tipping) is mixed with 1 µL of -cyano-4-hydroxycinnamic acid matrix solution (Agilent, Catalog #G2037A), and 1 µL of the mix is spotted on a MALDI sample plate. External calibration is performed using Calibration Mix 2 of Sequazyme Peptide Standards (PerSeptive Biosystems, Catalog #P2-3143-00). The sample's mass spectra are recorded in a reflection positive mode with an acceleration voltage of 20 kV. Biorad PDQuest 7.1 is used for image analysis to identify differentially expressed proteins. The peptide mass fingerprints are searched against NCBI NR database using the Mascot search engine. Events with little or no chitinase protein are selected for retransfection.

EXAMPLE 2

Figure 4:
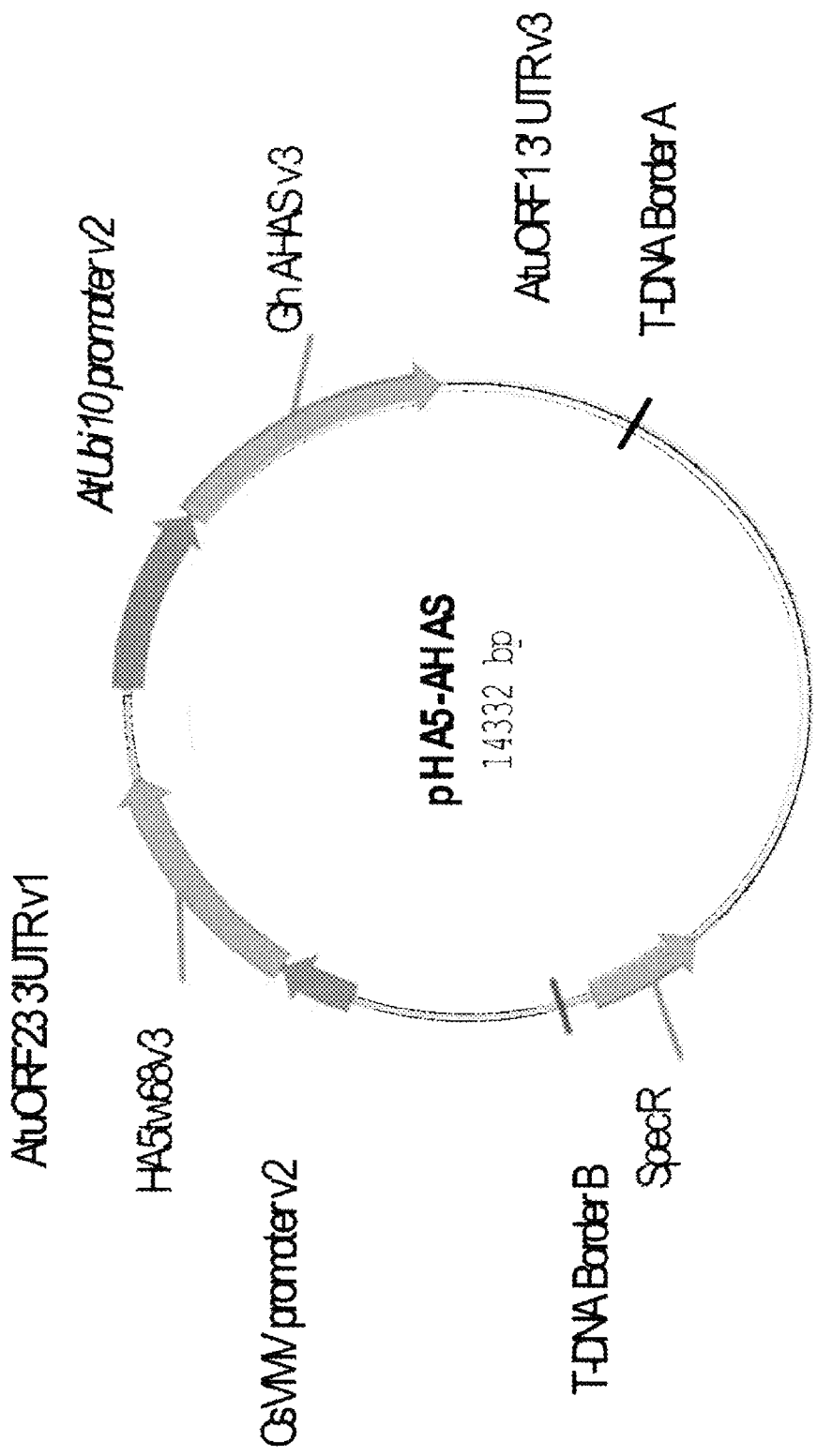
FIG. 4 is a schematic representation of plasmid pHA5-AHAS.
Figure 5:
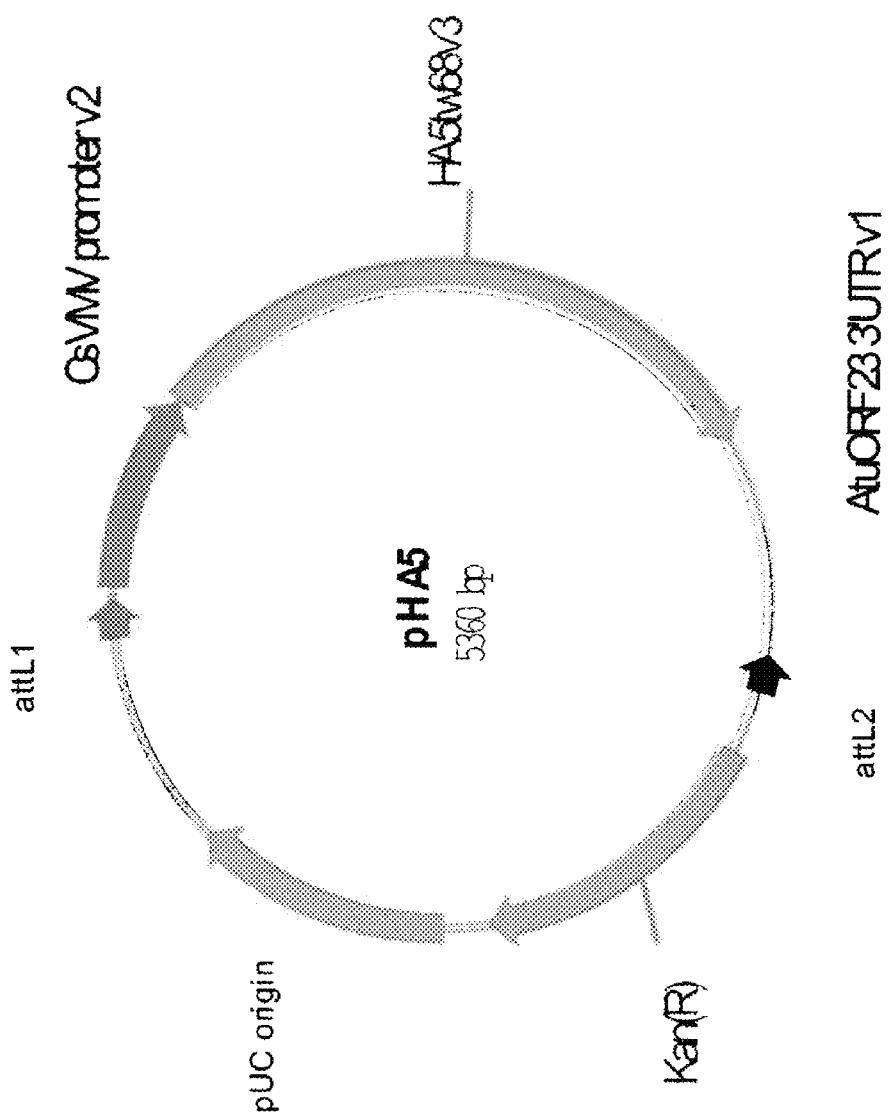
FIG. 5 is a schematic representation of plasmid pHA5.
Figure 6:
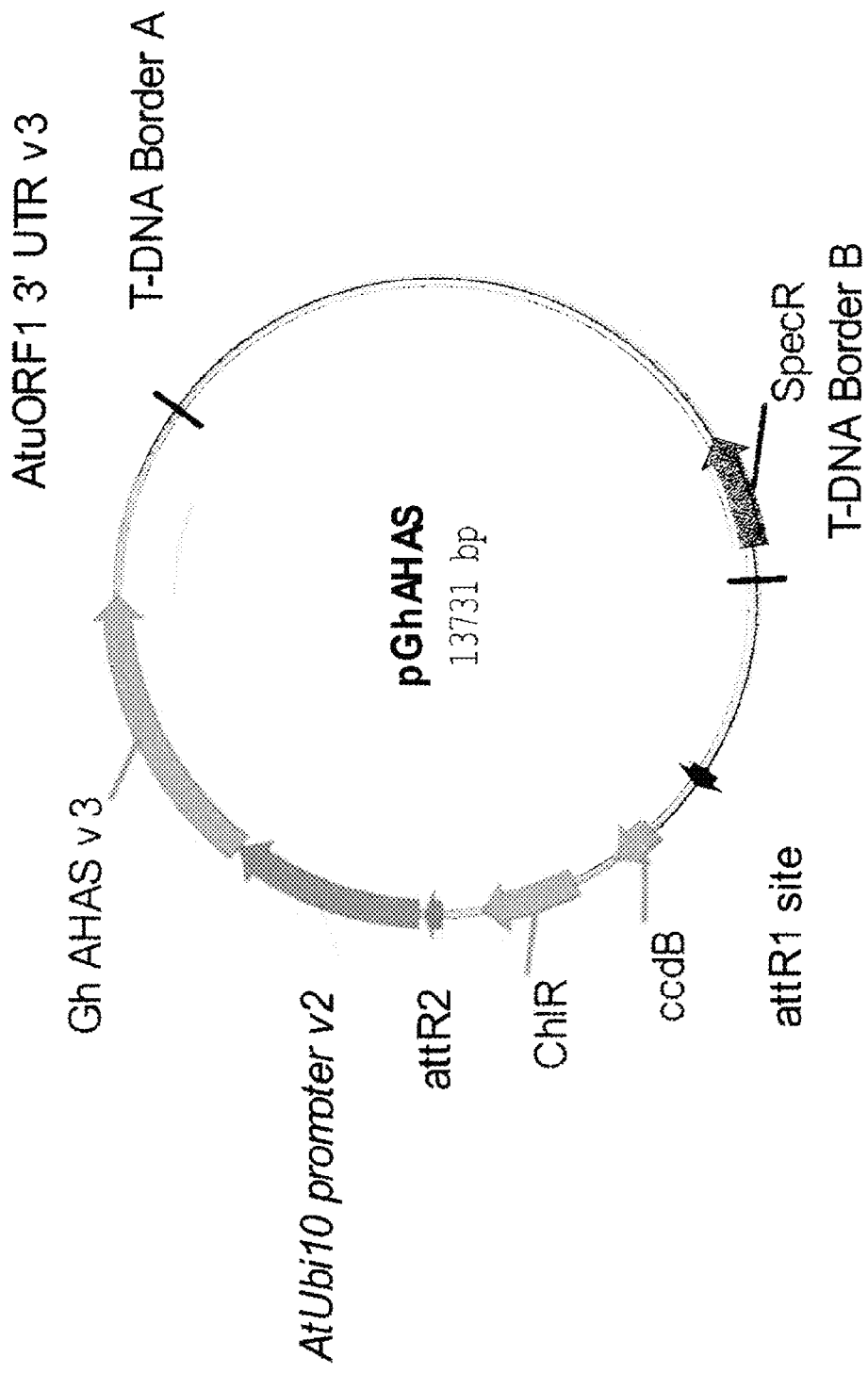
FIG. 6 is a schematic representation of plasmid pGhA-HAS.
Figure 7:
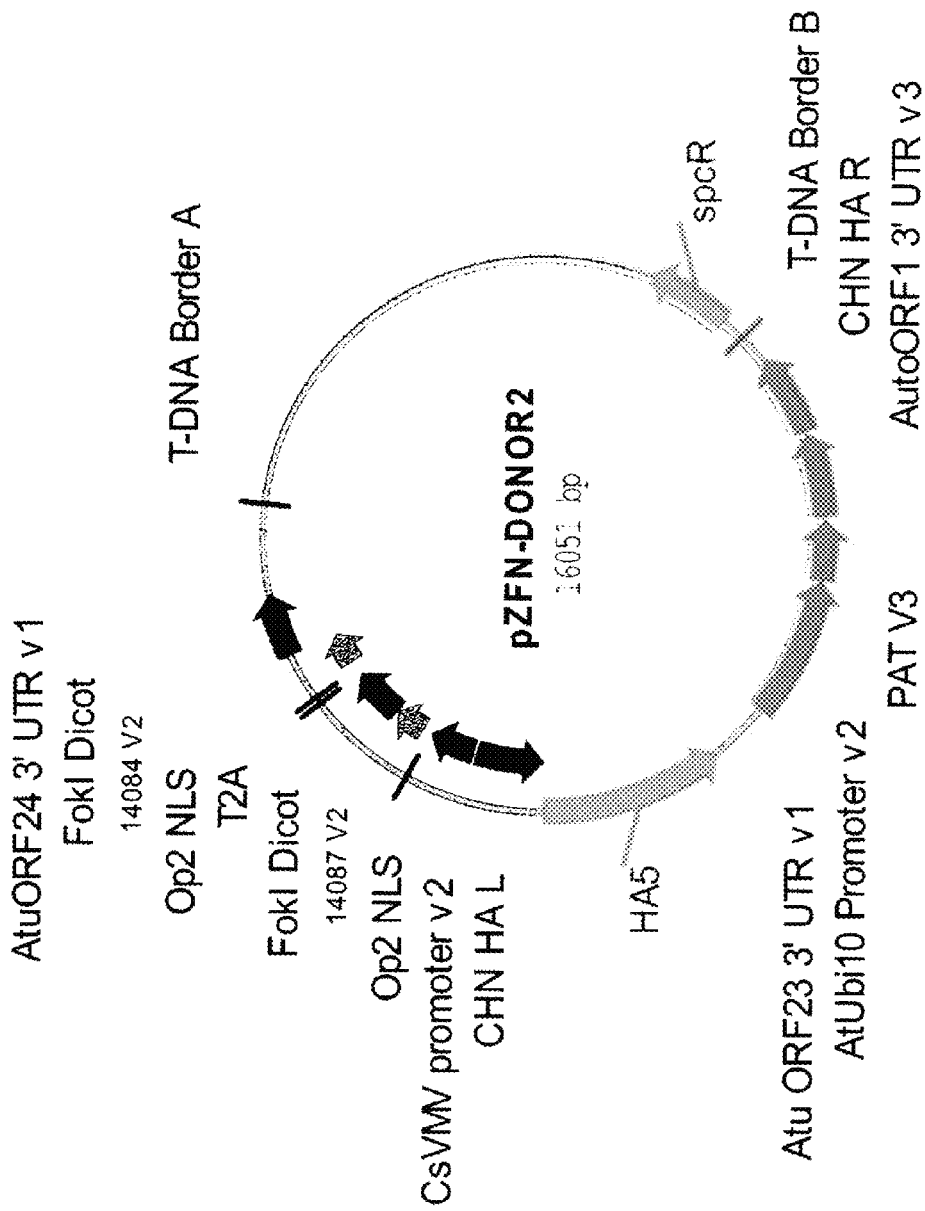
FIG. 7 is a schematic representation of plasmid pZFN-DONOR2.

Generation of HA5-Expressing Suspension Cultures from Endochitinase Knock-Down Culture Construction of HA5 Expression Vector pHA5-AHAS (FIG. 4) is a binary expression vector used for the re-transfection of the CHN50 endochitinase knock-down tobacco suspension culture. It contains a HA5tw68 gene (Garcia, et al., 1997, Virus Res. 51:115-124) driven by CsVMV promoter (Verdaguer et al., 1996, *Plant Molecular Biology* 31:1129-1139) and terminated by AtuORF23 3'UTR (Gelvin et al., 1987, EP222493), and a cotton AHAS-selectable marker gene (K. Rajasekaran, J. Grula, D. Anderson, 1996, *Plant Science* 119:115-124) driven by Ubi10 promoter (Callis, et al., 1990, *J Biol. Chem.* 265-12486-12493) and terminated by AtuORF1 3'UTR (Huang et al., *J. Bacteriol.* 172:1814-1822). pHA5-AHAS is cloned through a LR reaction of Gateway cloning technology using pHA5, a Gateway entry vector containing the HA5tw68 gene expression cassette (FIG. 5), and pAHAS, a Gateway destination vector containing the GhAHAS gene expression cassette (FIG. 6).

Generation of HA5-Expressing Transgenic Events

A cell suspension culture that has a PAT-selectable marker gene inserted into the λCHNSO endochitinase gene locus and with no or low endochitinase transcript and protein levels is maintained in LSBY2 media containing LS basal salts (PhytoTechnology Labs L689), 170 mg/L KH$_2$PO$_4$, 30 g/L sucrose, 0.2 mg/L 2,4-D, 0.6 mg/L thiamine-HCL and 15 mg/L BIALAPHOS® at a pH of 6.0. The cells are sub-cultured every seven days by adding 250 µl PCV to 50 mL of LSBY2 medium. The cultures are maintained in 250-mL flasks on a rotary shaker in the dark at 25+1° C. at 125 rpm.

In order to generate HAS-expressing cell cultures, a flask of a four-day post-sub-culture suspension culture is divided into 10-12 four mL aliquots and co-cultivated in 100×25 mm Petri dishes with 100 µL *Agrobacterium* strain LBA4404 harboring the pHA5-AHAS (FIG. 4) grown overnight to an $OD_{600}$~1.5. Dishes are wrapped with NESCOFILM® (Azwell Inc., Osaka, Japan) and incubated at 25° C. without shaking for three days after which 12 mL of LSBY2 medium containing 500 mg/L carbenicillin is added. Following re-suspension of the tobacco cells, 1 mL aliquots are dispensed onto 100×25 mm plates of LS-basal medium containing 500 mg/L carbenicillin and 1500 nM IMAZETHAPYR® solidified with 8 g/L TC agar, and incubated unwrapped at 28° C. in the dark. This resulted in 120-144 selection plates. Individual IMAZETHAPYR®-resistant isolates appear 10-14 days after plating and are transferred to individual 60×20 mm plates (one isolate per plate) where they are assigned a number and maintained under selection as callus on a 14-day sub-culture schedule until needed for analysis and subsequent suspension culture initiation.

The IMAZETHAPYR®-resistant transgenic events are subcultured onto fresh LS-basal medium containing 500 mg/L carbenicillin and 1500 nM IMAZETHAPYR® solidified with 8 g/L TC agar every two weeks for a total of three passages. Suspension cultures are initiated by transferring 500 mg of seven-day-old proliferating transgenic callus into a 125-mL flask containing 25 ml LS-basal medium containing 1500 nM IMAZETHAPYR®. The cells and liquid are mixed by pipetting three to five times with a 50 mL pipette to break up tissue then agitated on a shaker at 125 rpm in the dark at 25±1° C. The suspension cultures are subcultured on a weekly basis by transferring 125 µL of packed cells into 25 mL of fresh medium. The suspension cultures are maintained in 125-mL flasks on a rotary shaker in the dark at 25±1° C. at 125 rpm.

Event Selection for High HAS Protein Accumulation

Tissue samples are collected from transgenic events in duplicate at day 7 and day 14 after subculture. For each sample, 1 mL suspension volume is collected from a suspension culture using a 10 mL pipette. Samples are collected into 96-well cluster tube boxes (1.2 ml tubes, Costar, Corning, N.Y.). The suspension samples are allowed to settle on wet ice for ten minutes. Liquid media is aspirated from sample and discarded. Resulting cell pellet samples is frozen on dry ice and stored at −80° C.

At the time of analysis, samples are extracted in 0.1% DBDM (n-Dodecyl b-Dmaltoside, Sigma D4611) in PBS using a Kleco bead beater (Garcia Machine, Visalia, Calif.). Two steel BB's (Daisy 4.5 mm) are added to each tube along with 200 µl of DBDM-PBS. Samples are agitated at maximum speed for one minute followed by a five-minute centrifugation at 3000×g. Supernatants are removed to new tubes. The resulting pellet is re-extracted (200 µL buffer, one-minute agitation, five-minute spin). Supernatants from both extractions are pooled and used for analysis.

Samples are analyzed for HA5 expression by ELISA using a custom made ELISA kit (Beacon Analytical Systems, Portland, Me.). The kit contains plates that are double coated with first a donkey anti-chicken IgY antibody followed by a chicken anti-plant HA5 polyclonal antibody and blocked with BSA in PBS. Samples and standards (plant produced HA5 reference antigen) are loaded onto the plates and incubated for one hour. Following incubation, the plates are washed with PBST, tapped dry and an HRP-conjugated plant HA5 monoclonal antibody is added. The plates are incubated for 30 minutes before washing. A TMB substrate is added for 30 minutes before the reaction is stopped and the ODs are read. Test samples are quantified by linear regression against the quadratic curve generated for the plant reference antigen.

Cell Culture Scale-Up and Fermentation

Cultures accumulating the highest levels of HA5 protein are identified for scale-up. Suspension cultures of individual events are scaled up from a 25 mL working volume in a 125 mL Erlenmeyer flask to 70 mL and then 140 mL total volume in a 250 mL flask based on "flask-packed cell volume." Flask-packed cell volume is determined after a seven-day incubation period by aspirating a 10 mL sample under aseptic conditions from a well mixed flask into a serological pipette to a final volume of 10 mL. After 30 seconds of static settling, the volume of the cells in the pipette is multiplied by ten and recorded as the flask-packed cell volume to differentiate the measurement from a centrifugal-packed cell volume (PCV) measurement. The normal range for flash-packed cell volume is variable (15-60%) for individual events, but if a packed cell volume of ≥15% is not achieved within 14 days, the event is discontinued.

Culture maintenance and scale-up is performed by transferring cells from a seven-day flask to a final flash-packed cell volume of 5%. For cultures with a 50% packed cell volume, the inoculum transfer volume is 10% v/v. All Erlenmeyer flask cultures are incubated at 25±1° C. on an orbital shaker with a two-inch stroke length at 120 rpm for seven days. Fermentations utilizing the 2,800 mL Fernbach flask (working volume 1,000 mL) are conducted on an orbital incubator/shaker with a two-inch stroke length at 110 rpm for seven days at 25±1° C. Fermentations conducted in 101 Braun Biostat C ten-liter fermentors are initiated at an agitation speed of 200 rpm, an air flow of 4 liters per minute, and a vessel temperature of 26° C. Dissolved oxygen is maintained above 30% by a PID control loop that automatically increased the agitation rate between 200 and 450 rpm.

To assess and characterize the fermentor-grown cultures, in-process 10 mL samples are collected in 15 mL graduated centrifuge tubes under aseptic conditions at 24-hour intervals. Of each sample, 10 μL is struck for isolation on tryptic soy agar for assessment of foreign growth. Petri plates are incubated at 30° C. for two days, and then scored for the presence of bacterial or fungal growth. Samples containing foreign growth are verified by light microscopy at 1,000× magnification in subsequent sample collections. Fermentors that are verified to contain foreign growth are autoclaved and the cultures appropriately discarded.

The remainder of each fermentation sample is centrifuged at 2,500×g for ten minutes to separate the plant cells from the cell culture liquid. The PCV is determined by direct observation of the volume (mL) of packed cells in the tube following centrifugation. The final volume measurement is multiplied by ten and recorded as the PCV at the time point of collection. Approximately 3-4 mL of the clear supernatant phase from the tube is transferred into a 3 mL syringe and filtered (Corning PTFE #431231) into a clean 1.5 mL microcentrifuge tube. The contents of the tube are analyzed for glucose, pH, acetate, ortho-phosphate, ammonia, sodium, potassium, and lactate using the Bioprofile 300A Biochemistry Analyzer (Nova Biomedical, Boston, Mass.).

For total soluble protein and recombinant protein concentration, the remaining sample of supernatant and packed cells is treated by adding 2 to 3 mm stainless steel shot, and then placing the 15 mL sample tube in a Geno Grinder for two minutes at maximum agitation rate. The cell-free fraction is collected after centrifugation at 10,000 rpm for five minutes, and the pellet fraction is resuspended in a buffer consisting of PBS, pH 6.8, with 0.1% β-D-dodecyl maltoside. The resuspended pellet is placed back into the Geno Grinder and agitated for two minutes. Following centrifugation at 10,000 rpm for five minutes, the supernatant fractions are pooled and assayed for total soluble protein using the Bradford method. Extracts are also analyzed for HA5 protein.

Transgenic events are scaled to 10 L stirred tank reactors. Harvest criteria based on optimum volumetric productivity are developed based on changes in: (1) residual glucose in the fermentor, (2) packed cell volume, (3) respiratory gas analysis, (4) dissolved oxygen, and (5) pH. The optimum harvest time based on volumetric productivity occurs 46 hours after the depletion of glucose. The depletion of carbon source(s) correspond to an increase in pH from $5.90\pm0.12$–log $H^+$ to $6.5\pm0.24$–log $H^+$, a visible darkening of the fermentation broth, and a >85% reduction in respiratory activity as evidenced by oxygen uptake, carbon dioxide evolution, and dissolved oxygen.

EXAMPLE 3

Targeting the HA5 Gene to the Endochitinase Locus for High Level Expression

To take advantage of the regulatory machinery associated with high level endochitinase gene expression and protein accumulation in tobacco cell cultures, HA5 is precisely integrated in-frame using zinc finger-mediated gene targeting. An expression cassette containing zinc finger nuclease and PAT selectable marker gene cassettes along with HA5 coding region flanked by sequences homologous to the endogenous endochitinase gene is assembled (FIG. 7) and transfected into BY2 suspension culture cells as previously described using *Agrobacterium*-mediated delivery and BIALAPHOS® selection. Transgenic events are then screened for targeted integration using 3' and 5'-"in-out" PCR analysis of genomic DNA as previously described. Targeted events are selected for HA5 protein production and scaled up as previously described.

While a number of exemplary aspects and embodiments have been discussed above, those of skill in the art will recognize certain modifications, permutations, additions and sub-combinations thereof. It is, therefore, intended that the following appended claims and claims hereafter introduced are interpreted to include all such modifications, permutations, additions and sub-combinations as are within their true spirit and scope.

All references, including publications, patents, and patent applications, cited herein are hereby incorporated by reference to the same extent as if each reference is individually and specifically indicated to be incorporated by reference and is set forth in its entirety herein. The references discussed herein are provided solely for their disclosure prior to the filing date of the present application. Nothing herein is to be construed as an admission that the inventors are not entitled to antedate such disclosure by virtue of prior invention.

What is claimed is:

1. A method of producing a protein of interest, the method comprising:

providing a plant cell comprising a first nucleic acid molecule comprising a first nucleotide genomic sequence encoding a first protein selected from the group consisting of the wound-induced protein (WIP) and osmotin;

providing to the plant cell at least one zinc finger nuclease (ZFN) capable of inducing a double-strand break at a cleavage site in the first nucleotide sequence in a region encoding the first protein, so as to cleave the first nucleic acid molecule with the at least one ZFN to generate a double-strand break at the cleavage site;

providing to the plant cell a second nucleic acid molecule comprising a second nucleotide sequence, so as to repair the double-strand break through insertion of the second nucleotide sequence at the cleavage site, wherein inserting the second nucleotide sequence into the cleavage site decreases expression of the first protein;

providing to the plant cell a third nucleic acid molecule comprising a third nucleotide sequence, wherein the third nucleotide sequence encodes a protein of interest; and expressing the protein of interest from the third nucleotide sequence.

2. The method according to claim 1, wherein the third nucleotide sequence is inserted into the genome of the plant cell.

3. The method according to claim 1, wherein the plant cell is from a dicotyledonous plant species.

4. The method according to claim 3, wherein the dicotyledonous plant species is selected from the group consisting of an *Arabidopsis* species, sunflower, cotton, rapeseed, tobacco, peanut, and soybean.

5. The method according to claim 4, wherein the dicotyledonous plant species is a tobacco species of the genus, *Nicotiana*.

6. The method according to claim 1, wherein the plant cell is from a monocotyledonous plant species.

7. The method according to claim 6, wherein the monocotyledonous plant species is selected from the group consisting of maize, rice, sugarcane, and wheat.

8. The method according to claim 1, wherein inserting the second nucleotide sequence into the cleavage site comprises homologous recombination, SDSA, or a nucleic acid break repair mechanism.

9. The method according to claim 8, wherein the third nucleotide sequence is inserted into the genome of the plant cell.

10. A method of producing a protein of interest, the method comprising:
    providing a plant cell comprising a first nucleic acid molecule comprising a first genomic nucleotide sequence encoding a first protein selected from the group consisting of the wound-induced protein (WIP) and osmotin;
    providing the plant cell at least one zinc finger nuclease (ZFN) capable of inducing a double-strand break at a cleavage site in the first nucleotide sequence in a region encoding the first protein, so as to cleave the first nucleic acid molecule with the at least one ZFN to generate a double-strand break at the cleavage site;
    providing to the plant cell a second nucleic acid molecule comprising a second nucleotide sequence encoding a protein of interest, so as to repair the double-strand break through the insertion of the second nucleotide sequence at the cleavage site, wherein inserting the second nucleotide sequence into the first nucleotide sequence decreases expression of the first protein; and
    expressing the protein of interest.

11. The method according to claim 10, wherein the expression of the protein of interest is at least partially regulated by the regulatory elements that regulated expression of the first protein from the first nucleotide sequence before generation of the double-strand break in the first nucleotide sequence.

12. The method according to claim 10, wherein the plant cell is from a dicotyledonous plant species.

13. The method according to claim 12, wherein the dicotyledonous plant species is selected from the group consisting of an *Arabidopsis* species, sunflower, cotton, rapeseed, tobacco, peanut, and soybean.

14. The method according to claim 13, wherein the dicotyledonous plant species is a tobacco species of the genus, *Nicotiana*.

15. The method according to claim 10, wherein the plant cell is from a monocotyledonous plant species.

16. The method according to claim 15, wherein the monocotyledonous plant species is selected from the group consisting of maize, rice, and wheat.

17. The method according to claim 10, wherein inserting the second nucleotide sequence into the cleavage site comprises heterologous recombination, SDSA, or nucleic acid break repair mechanism.

18. A method of producing a protein of interest, the method comprising:
    providing a plant cell comprising a first nucleic acid molecule comprising a first genomic nucleotide sequence encoding a first protein selected from the group consisting of the wound-induced protein (WIP) and osmotin;
    providing to the plant cell at least one first zinc finger nuclease (ZFN) capable of inducing a double-strand break site in the first nucleotide sequence encoding the first protein at a first cleavage site, so as to generate a first double-strand break at the first cleavage site;
    providing to the plant cell at least one second ZFN capable of inducing a double-strand break in the first nucleotide sequence encoding the first protein at a second cleavage site, so as to generate a second double-strand break at the second cleavage site, wherein the first and second double-strand breaks are repaired, thereby excising the portion of the first nucleotide sequence between the first and second double-strand breaks and decreasing expression of the first protein;
    providing to the plant cell a second nucleic acid molecule comprising a second nucleotide sequence encoding a protein of interest; and
    expressing the protein of interest.

19. The method according to claim 18, wherein repairing the first and second double-strand breaks comprises inserting the second nucleotide sequence between the first and second cleavage sites, in place of the excised portion of the first nucleotide sequence.

20. The method according to claim 19, wherein the expression of the protein of interest is at least partially regulated by the regulatory elements that regulated expression of the first protein.

21. The method according to claim 18, wherein the plant cell is from a dicotyledonous plant species.

22. The method according to claim 21, wherein the dicotyledonous plant species is selected from the group consisting of an *Arabidopsis* species, sunflower, cotton, rapeseed, tobacco, peanut, and soybean.

23. The method according to claim 22, wherein the dicotyledonous plant species is a tobacco species of the genus, *Nicotiana*.

24. The method according to claim 18, wherein the plant cell is from a monocotyledonous plant species.

25. The method according to claim 24, wherein the monocotyledonous plant species is selected from the group consisting of maize, rice, sugarcane, and wheat.

26. The method according to claim 19, wherein inserting the second nucleotide sequence between the first and second cleavage sites, in place of the excised portion of the first nucleotide sequence comprises:
    homologous recombination, SDSA, or a nucleic acid break repair mechanism.

* * * * *